United States Patent
Newberry

(10) Patent No.: US 10,500,354 B2
(45) Date of Patent: Dec. 10, 2019

(54) SYSTEM AND METHOD FOR ATOMIZING AND MONITORING A DRUG CARTRIDGE DURING INHALATION TREATMENTS

(71) Applicant: Sanmina Corporation, San Jose, CA (US)

(72) Inventor: Robert Steven Newberry, New Hope, AL (US)

(73) Assignee: SANMINA CORPORATION, San Jose, CA (US)

(*) Notice: Subject to any disclaimer, the term of this patent is extended or adjusted under 35 U.S.C. 154(b) by 330 days.

(21) Appl. No.: 15/462,700

(22) Filed: Mar. 17, 2017

(65) Prior Publication Data

US 2017/0189629 A1 Jul. 6, 2017

Related U.S. Application Data

(63) Continuation-in-part of application No. 14/866,500, filed on Sep. 25, 2015, now Pat. No. 10,321,860, and
(Continued)

(51) Int. Cl.
| | |
|---|---|
| *A61M 11/04* | (2006.01) |
| *A61M 15/00* | (2006.01) |
| *A24F 47/00* | (2006.01) |

(52) U.S. Cl.
CPC ...... *A61M 11/041* (2013.01); *A61M 15/0021* (2014.02); *A61M 15/0028* (2013.01);
(Continued)

(58) Field of Classification Search
CPC ............ A61M 11/041; A61M 15/0021; A61M 2230/40; A61M 2230/42; A61B 5/0816;
(Continued)

(56) References Cited

U.S. PATENT DOCUMENTS

| | | |
|---|---|---|
| 7,017,829 B2 | 3/2006 | Martens, III et al. |
| 7,350,720 B2 | 4/2008 | Jaworski et al. |

(Continued)

FOREIGN PATENT DOCUMENTS

| | | |
|---|---|---|
| EP | 2460423 | 6/2012 |
| WO | 03/059424 | 7/2003 |

(Continued)

OTHER PUBLICATIONS

International Search Report & Written Opinion PCT/US17/0230077 dated Sep. 12, 2017; 25 pages.
(Continued)

*Primary Examiner* — Nathan R Price
*Assistant Examiner* — Dung T Ulsh
(74) *Attorney, Agent, or Firm* — Loza & Loza, LLP; Julio M. Loza; Jessica W. Smith

(57) ABSTRACT

An atomizer includes a cartridge with a reservoir containing a fluid and a heating system configured to atomize the fluid into a vapor for inhalation. A respiratory indicator is configured to determine an inhalation period and an exhalation period of a patient using the atomizer. The atomizer then increases atomization of the vapor during the inhalation period and decreases atomization of the vapor during the exhalation period. An impedance sensor measures an amount of the fluid in the atomizer and deactivates atomization in response to an indication of a low fluid level.

30 Claims, 25 Drawing Sheets

Related U.S. Application Data a continuation-in-part of application No. 15/275,388, filed on Sep. 24, 2016, now Pat. No. 9,642,578, and a continuation-in-part of application No. 15/275,444, filed on Sep. 25, 2016, now Pat. No. 9,642,538, and a continuation-in-part of application No. 15/276,760, filed on Sep. 26, 2016, now Pat. No. 9,636,457, and a continuation-in-part of application No. 15/400,916, filed on Jan. 6, 2017, and a continuation-in-part of application No. 15/404,117, filed on Jan. 11, 2017.

(60) Provisional application No. 62/457,138, filed on Feb. 9, 2017, provisional application No. 62/463,104, filed on Feb. 24, 2017.

(52) U.S. Cl.
CPC ...... *A24F 47/00* (2013.01); *A61M 2205/3379* (2013.01); *A61M 2205/3584* (2013.01); *A61M 2206/14* (2013.01); *A61M 2230/005* (2013.01); *A61M 2230/04* (2013.01); *A61M 2230/20* (2013.01); *A61M 2230/30* (2013.01); *A61M 2230/42* (2013.01)

(58) Field of Classification Search
CPC ..... A61B 5/087; A61B 5/0826; A61B 5/0873; A61B 5/4818; A61B 5/1455
See application file for complete search history.

(56) References Cited

U.S. PATENT DOCUMENTS

| | | |
|---|---|---|
| 7,775,459 B2 | 8/2010 | Martens, III et al. |
| 8,868,245 B2 | 10/2014 | Luc et al. |
| 2005/0177137 A1* | 8/2005 | Kipfer ............... A61M 5/14244 604/890.1 |
| 2005/0279854 A1 | 12/2005 | Martens, III et al. |
| 2007/0144514 A1 | 6/2007 | Yeates et al. |
| 2008/0142002 A1 | 6/2008 | Fink et al. |
| 2010/0168739 A1* | 7/2010 | Wu .................... A61B 18/1492 606/41 |
| 2010/0313883 A1* | 12/2010 | Von Hollen ......... A61M 11/005 128/200.16 |
| 2011/0040574 A1* | 2/2011 | Fung .................... A61B 5/0205 705/2 |
| 2012/0291791 A1 | 11/2012 | Pradeep |
| 2014/0283931 A1* | 9/2014 | Zaro .................. G01F 23/2962 137/558 |
| 2015/0265347 A1* | 9/2015 | Yates .................... A61B 18/18 606/50 |
| 2015/0366492 A1* | 12/2015 | De Haan ............. A61B 5/1455 600/323 |
| 2016/0022209 A1* | 1/2016 | Fraisl ........................ A45F 3/16 600/590 |
| 2016/0255878 A1 | 9/2016 | Huang et al. |
| 2017/0027226 A1* | 2/2017 | Mironov ............... A24F 47/008 |
| 2017/0042236 A1 | 2/2017 | Gorilovsky |
| 2018/0007960 A1* | 1/2018 | Suzuki .................... A24F 47/00 |
| 2018/0020979 A1* | 1/2018 | Wagner ............. A61B 5/14552 600/379 |

FOREIGN PATENT DOCUMENTS

| | | |
|---|---|---|
| WO | 2008116165 | 9/2008 |
| WO | 2012026963 | 3/2012 |
| WO | 2015015431 | 2/2015 |
| WO | WO2015175527 | 11/2015 |
| WO | 2016001922 | 1/2016 |
| WO | 2017055795 | 4/2017 |

OTHER PUBLICATIONS

International Search Report & Invitation to Pay Additional Fees for PCT/US17/0230077 dated Jul. 3, 2017; 19 pages.

\* cited by examiner

```
                    ┌─ 2200

┌──────────────────────────────────────┐
│  MONITOR CONCENTRATION OF RELEVANT   │
│  SUBSTANCES IN ARTERIAL BLOOD FLOW AND/OR │─ 2202
│              TISSUE                  │
└──────────────────┬───────────────────┘
                   ▼
┌──────────────────────────────────────┐
│     MONITOR PATIENT VITALS AND       │─ 2204
│       OTHER BIOSENSOR DATA           │
└──────────────────┬───────────────────┘
                   ▼
┌──────────────────────────────────────┐
│ DETECT PREDETERMINED THRESHOLD IN ONE│
│ OR MORE MEASUREMENTS OF THE PATIENT  │─ 2206
│   VITALS OR OTHER BIOSENSOR DATA     │
└──────────────────┬───────────────────┘
                   ▼
┌──────────────────────────────────────┐
│     DEACTIVATE OPERATION OF ATOMIZER │─ 2208
└──────────────────────────────────────┘
```

FIG. 22

SYSTEM AND METHOD FOR ATOMIZING AND MONITORING A DRUG CARTRIDGE DURING INHALATION TREATMENTS

CLAIM OF PRIORITY UNDER 35 U.S.C. § 119 AND $120

The present application claims priority under 35 U.S.C. § 119 to U.S. Provisional Application No. 62/457,138 entitled, "SYSTEM AND METHOD FOR ATOMIZING AND MONITORING A DRUG CARTRIDGE DURING INHALATION TREATMENTS," filed Feb. 9, 2017, and hereby expressly incorporated by reference herein.

The present application claims priority under 35 U.S.C. § 119 to U.S. Provisional Application No. 62/463,104 entitled, "SYSTEM AND METHOD FOR MONITORING NITRIC OXIDE LEVELS USING A NON-INVASIVE, MULTI-BAND BIOSENSOR 500," filed Feb. 24, 2017, and hereby expressly incorporated by reference herein.

The present application claims priority under 35 U.S.C. § 120 as a continuation in part to U.S. patent application Ser. No. 14/866,500 entitled, "SYSTEM AND METHOD FOR GLUCOSE MONITORING," filed Sep. 25, 2015, and hereby expressly incorporated by reference herein.

The present application claims priority under 35 U.S.C. § 120 as a continuation in part application to U.S. patent application Ser. No. 15/275,388 entitled, "SYSTEM AND METHOD FOR HEALTH MONITORING USING A NON-INVASIVE, MULTI-BAND BIOSENSOR 500," filed Sep. 24, 2016 and hereby expressly incorporated by reference herein.

The present application claims priority under 35 U.S.C. § 120 as a continuation in part application to U.S. patent application Ser. No. 15/275,444 entitled, "SYSTEM AND METHOD FOR A BIOSENSOR 500 MONITORING AND TRACKING BAND," filed Sep. 25, 2016 and hereby expressly incorporated by reference herein.

The present application claims priority under 35 U.S.C. § 120 as a continuation in part application to U.S. patent application Ser. No. 15/276,760 entitled, "SYSTEM AND METHOD FOR A DRUG DELIVERY AND BIOSENSOR 500 PATCH," filed Sep. 26, 2016 and hereby expressly incorporated by reference herein.

The present application claims priority under 35 U.S.C. § 120 as a continuation in part application to U.S. patent application Ser. No. 15/400,916 entitled, "SYSTEM AND METHOD FOR HEALTH MONITORING INCLUDING A REMOTE DEVICE," filed Jan. 6, 2017 and hereby expressly incorporated by reference herein.

The present application claims priority under 35 U.S.C. § 120 as a continuation in part application to U.S. patent application Ser. No. 15/404,117 entitled, "SYSTEM AND METHOD FOR HEALTH MONITORING INCLUDING A USER DEVICE AND BIOSENSOR 500," filed Jan. 11, 2017 and hereby expressly incorporated by reference herein.

FIELD

This application relates to systems and methods for atomization of liquids and more particularly to systems and methods for supplying liquid by a wick to be atomized in a refillable cartridge.

BACKGROUND

Vaporized drugs are commonly administered to treat patients in a home, hospital, or other healthcare facilities. Typically atomized sprays are used for over the counter medications. However, these solutions do not reach far beyond the nasal cavity and may leak medicine during periods of storage.

In addition, the patient's vitals, such as temperature, blood oxygen levels, blood pressure, respiration, etc., may need to be monitored periodically typically using one or more additional instruments. For example, additional instruments for obtaining vitals of a patient include blood pressure cuffs, thermometers, $S_{O2}$ measurement devices, blood tests, etc. Often, multiple instruments must be brought to a patient's room by a caretaker and the measurements collected by each instrument. This monitoring process can be time consuming, inconvenient and is not always continuous. It may also disrupt sleep of the patient. The measurements of the vitals must then be manually recorded into the patient's electronic medical record.

As such, there is a need for an improved system and method that includes a non-invasive, continuous health monitoring system that can be used in combination with an atomized drug delivery system.

SUMMARY

According to a first aspect, an atomizer comprises a cartridge configured to hold a fluid and an atomizer system configured to atomize the fluid in the cartridge into a vapor for inhalation. A respiratory indicator is configured to determine a respiration rate or inhalation and exhalation period. A processing circuit is configured to control the atomizer system to increase atomization of the vapor during an inhalation period and decrease atomization of the vapor during an exhalation period. The atomizer may further include a fluid sensor configured to detect an indicator of an amount of fluid in the cartridge. The processing circuit may be further configured to determine the indicator of the amount of fluid in the cartridge reaches a predetermined level and deactivate the atomizer system in response to the indicator of the amount of fluid in the cartridge reaching the predetermined level.

According to a second aspect, an atomizer comprises a cartridge configured to hold a fluid and an atomizer system configured to atomize the fluid in the cartridge into a vapor for inhalation. The atomizer system includes a wick for absorbing fluid in the cartridge and a heating element in contact with the wick, wherein the heating element increases in heat to atomize the fluid absorbed by the wick. An impedance sensor is configured to detect an indicator of an amount of fluid in the cartridge using the heating element. A processing circuit may be configured to activate the atomization system to operate in the atomization mode to atomize the fluid in the cartridge into a vapor using the heating element, deactivate the atomization system, and activate the impedance sensor to detect the impedance of the wick using the heating element.

According to a third aspect, an atomizer comprises a cartridge configured to hold a fluid and an atomizer system configured to atomize the fluid in the cartridge into a vapor for inhalation. A biosensor is integrated on the atomizer and is configured to obtain a respiratory rate using a spectral response. A processing circuit is configured to control the atomizer system to increase atomization of the vapor during an inhalation period and decrease atomization of the vapor during an exhalation period. The biosensor is further configured to monitor vitals of a patient, wherein the patient vitals includes one or more of: respiratory rate, heart rate or blood pressure. The biosensor may further monitor a concentration of a substance in arterial blood flow of the patient and an absorption rate of the substance in the surrounding tissue.

BRIEF DESCRIPTION OF THE DRAWINGS

FIG. 22 illustrates a logical flow diagram of an exemplary method of operation of the atomizer using the biosensor.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Embodiments of the atomizer and components thereof described herein may be included in any type of device for reducing a liquid to a spray or vapor. For example, the atomizer described herein may deliver medicine from a liquid state into a fine spray of aerosols to be inhaled through the nose and/or mouth, either directly or through a mask. The atomizer may also be used to deliver non-medicinal substances, such as nicotine based products. The atomizer may also be used to generate a vapor for disinfecting, cooling or spraying a perfume into the air.

Figure 1:
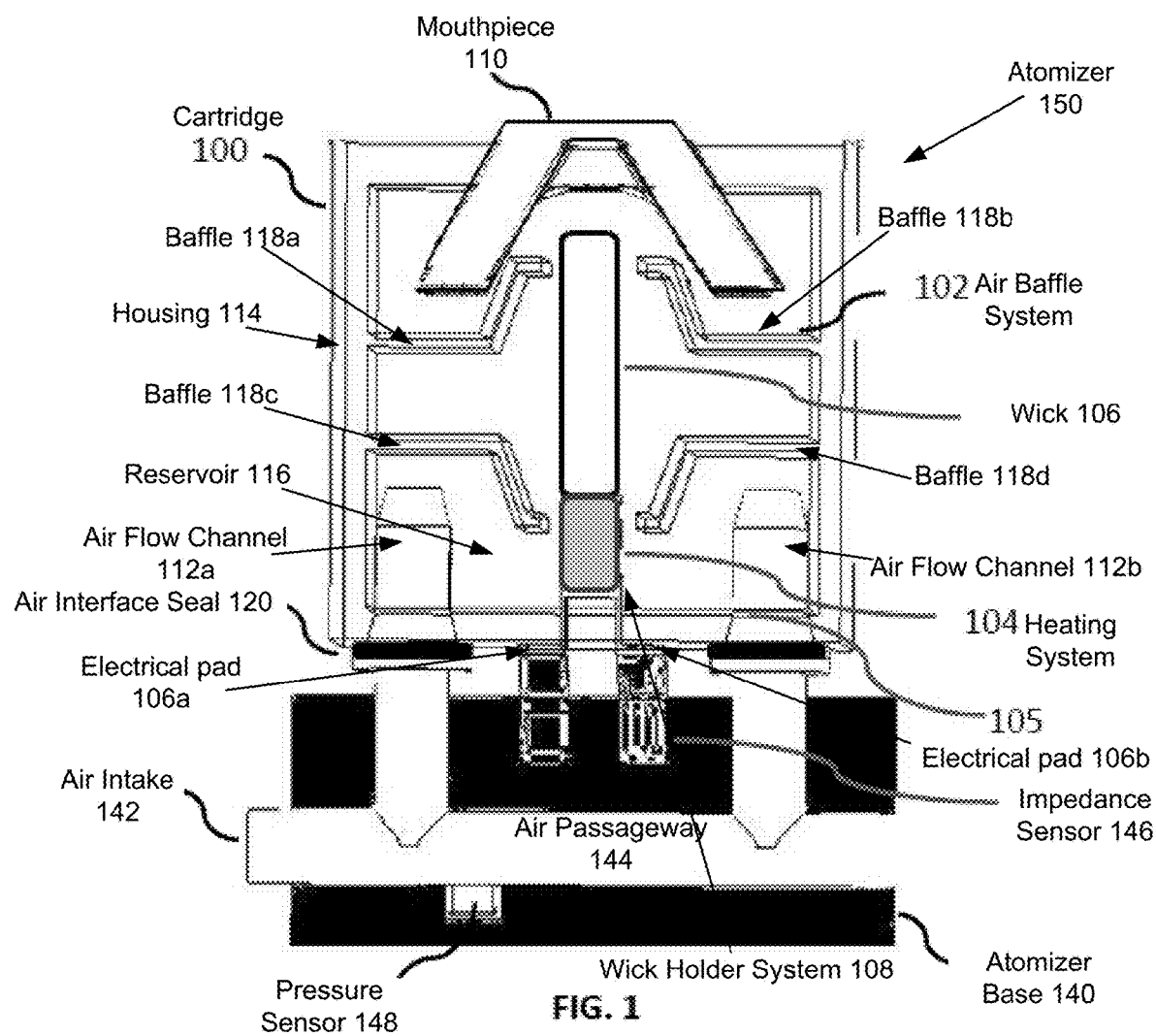
FIG. 1 illustrates a schematic block diagram of an embodiment of an atomizer including a cartridge and atomizer base.

FIG. 1 illustrates a schematic block diagram of an embodiment of an atomizer 150 including a cartridge 100 and atomizer base 140. In one aspect, the cartridge 100 is replaceably mounted to the atomizer base 140 such that the cartridge 100 may be removed and replaced with another new cartridge. In another aspect, the cartridge 100 may be refillable.

The cartridge 100 includes an air baffle system 102, heating element 104, wick 106, wick holder system 108, mouth piece 110, and airflow channels 112*a*, 112*b*. The cartridge 100 comprises a housing 114 that forms a fluid reservoir 116. The fluid reservoir 116 holds a fluid for atomization, such as a medicinal substance, drug, nicotine product, etc. One or more baffles 118 of the air baffle system 102 protrude into the fluid reservoir 116 from the housing 114. The baffles 118 may be attached to the housing 114 or formed by the housing 114.

The wick 106 extends from a bottom portion of the fluid reservoir 116 between one or more sets of baffles 118. A first set of baffles 118*a*, 118*b* protrude across one or more openings to the mouthpiece 110 towards the wick 106. The first set of baffles 118*a*, 188*b* create two air chambers in the cartridge 100, wherein each chamber includes at least one opening to the mouthpiece 110. The two chambers form a dual channel air flow path for enhanced delivery of the atomized vapors into deep lung areas. The baffles 118*a,b* also help prevent liquid or large droplets from entering the mouthpiece 110. A second set of baffles 118*c*, 118*d* protrude across air flow channels 112a, 112b towards the wick to help prevent atomized vapors from escaping into the air flow channels 112a, 112b.

The air flow channels 112a, 112b each include an air interface seal 120 constructed for removal and replacement of the cartridge 100 from the atomizer base 140. When the cartridge 100 is mounted on the atomizer base 140, the air interface seal 120 is broken and allows air flow between an air intake 142 in the atomizer base 140 into the air flow channels 112a, 112b. A pressure sensor 148 is configured to measure the air flow between the air intake 142 and the air flow channels 112a, 112b. The air channels 109 allow the pressure sensor 108 to detect both inhalation and exhalation cycles by measure the air pressure. The air flow inside the drug delivery device includes outside air ports to allow a proper flow of air from the drug delivery device into the drug cartridge 100 and channels the air into the two prong mouth piece 101 towards the user.

Figure 2:
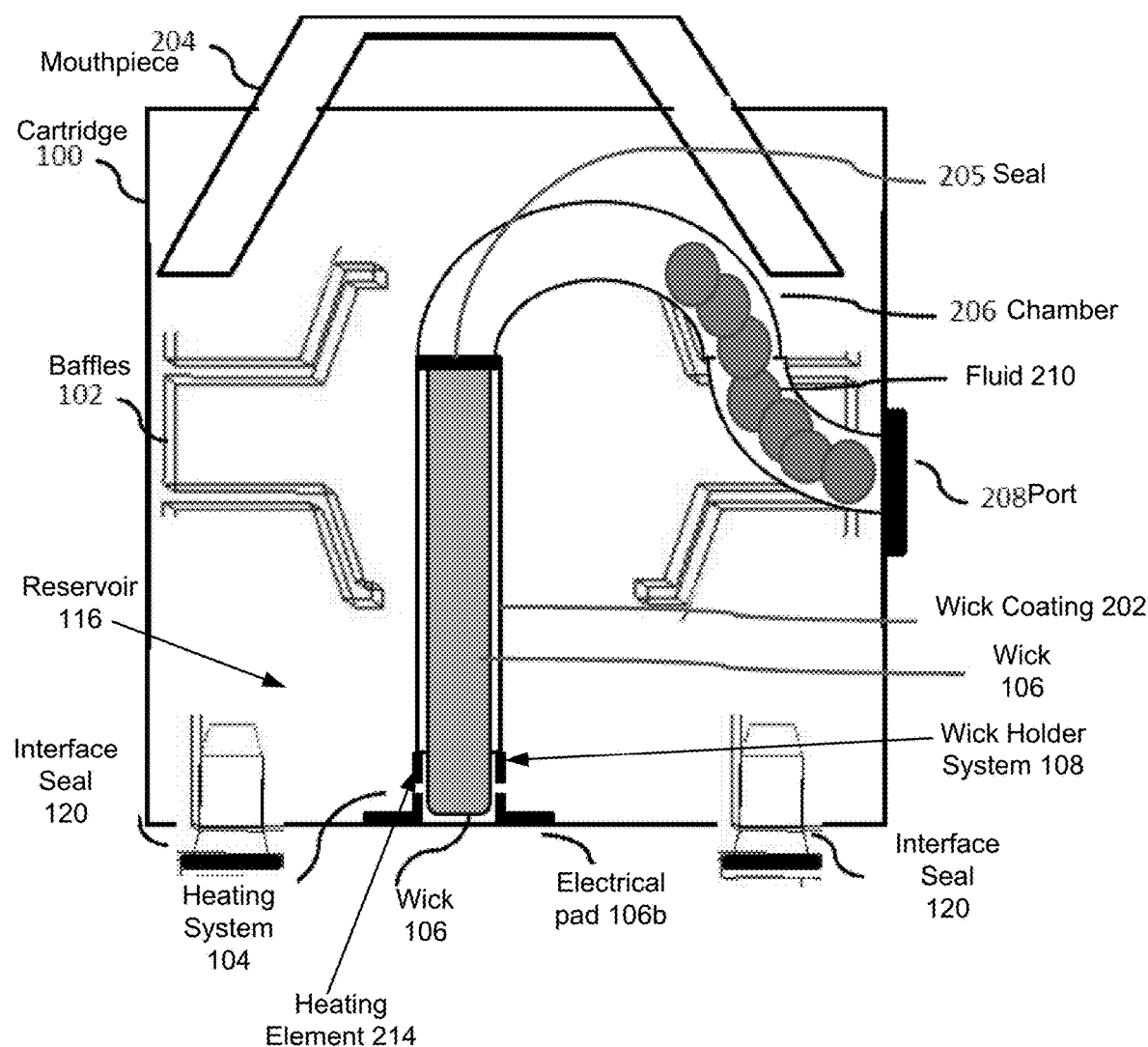
FIG. 2 illustrates a schematic block diagram of an embodiment of the atomizer including a soluble seal system.

FIG. 2 illustrates a schematic block diagram of an embodiment of the atomizer 150 including a soluble seal system. The soluble seal system includes a wick coating 202 that coats the wick 106. The wick coating 202 may be applied by saturating or dosing the wick in a heat soluble material. Preferably, the material is inert in water or in the fluid in the reservoir but melts away in the presence of heat. The wick 106 may be pre-coated in the soluble material during manufacture. The soluble seal system further includes a seal 204 on the upper portion of the wick 106. The seal 204 separates the wick 106 from an upper chamber 206. The upper chamber 206 extends from the seal 204 to a port 208 in the housing 114. The fluid 210 remains sealed in the upper chamber 206 until activation of the atomizer 100.

During manufacture, the wick 200 is pre-soaked with a coating, e.g. with either medicine or vapor release aqueous substance like water that enhances mixing of the fluid with the wick 106 during a treatment. The coated wick 200 is inserted into the reservoir 116, and the seal 205 is positioned over the wick 106 in the upper chamber 206. Fluid or other solid or gaseous substance 210 is then inserted into the upper chamber 206 through the port 208, and the port 208 is then sealed. For example, the port 208 may be sealed via ultrasonic welding, fasteners, glues or epoxies, laser welding, or forced insertion of compression materials to be used a sealing gasket methods. The port 208 can also be constructed with microfiber materials configured to allow air flow into the chamber 206 but not outside liquids such as water.

The fluid 210 may not penetrate the seal 205. The fluid 210 is thus contained within the upper chamber 206 in the reservoir 116 during shipment and storage. The wick 200 is intended to be inserted into the drug chamber device 206 only during manufacturing. The pre-coated wick 106 is inserted into the cartridge 100 with sealing material which will set during manufacturing assembly of the cartridge 100. Afterward the drug or medicine intended for treatment will be inserted via port 208 located on the drug cartridge 100 and sealed.

The chamber 206 helps to prevent spilling of the fluid 210 from the cartridge 100 or exposure of the fluid 210 before activation. The chamber 206 also helps to provide a clean or sterile environment to help prevent contamination of the fluid 210.

In use, the cartridge 100 is inserted into the atomizer base 140, and the heating system 104 is activated. The heating system 104 heats the wick 106 and melts or vaporizes the wick coating 202 and the seal 205. The fluid 210 may then penetrate the wick 106 and flow into the reservoir 116.

During the initial heat cycle of the wick 106, the interface seal 205 will break down and allow the fluid 210 to intermix with the wick 106. The atomizer 150 is then operable to provide atomized vapors during the heating cycle when activating the heating element 214. The soluble seal system thus seals a chamber 206 that holds the fluid 210 and helps prevent spilling of the fluid 210. The soluble seal system then releases the fluid 210 after activation of the heating system 104.

Figure 3:
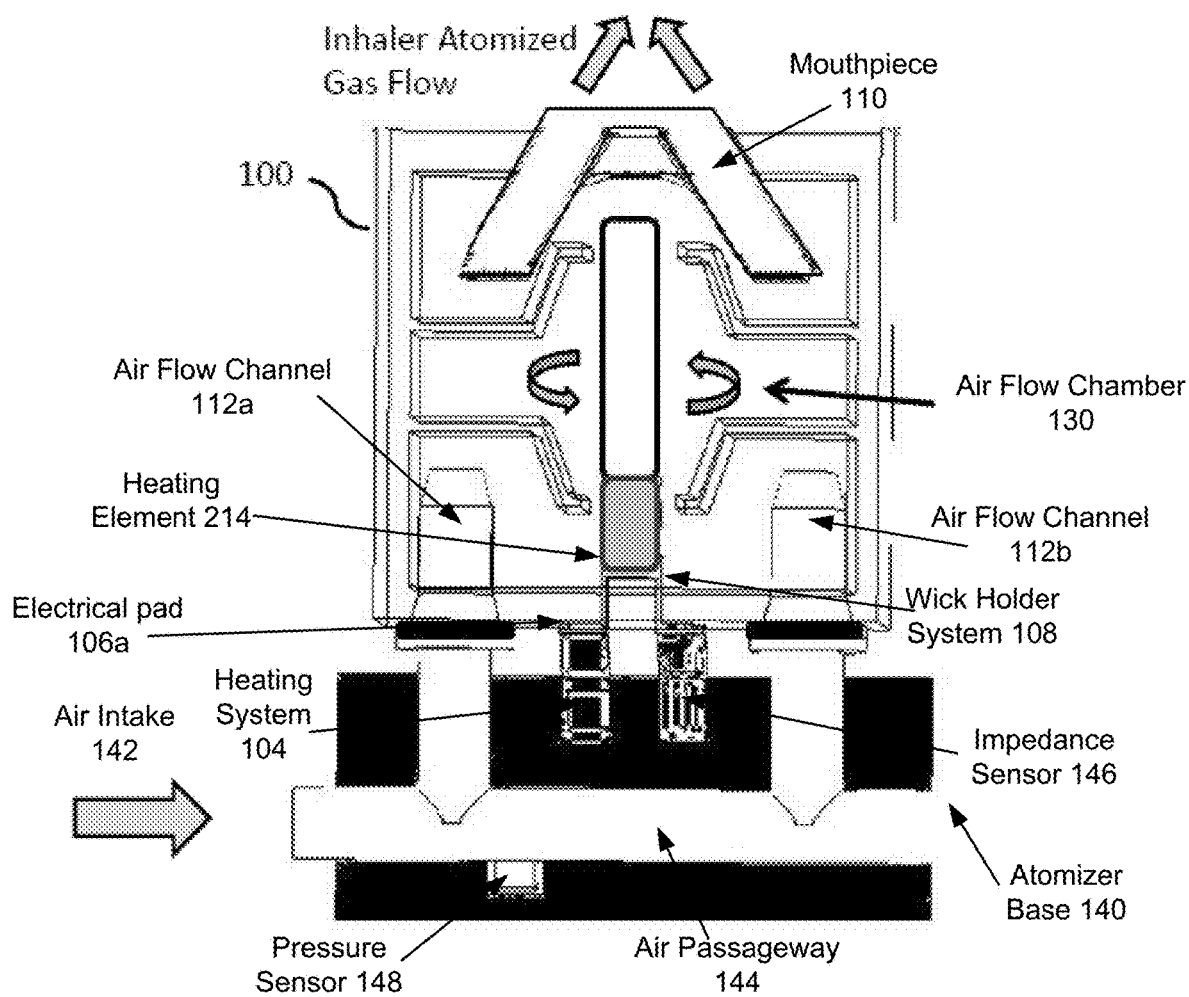
FIG. 3 illustrates a schematic block diagram of an embodiment of the atomizer including a respiration activation system.
Figure 4:
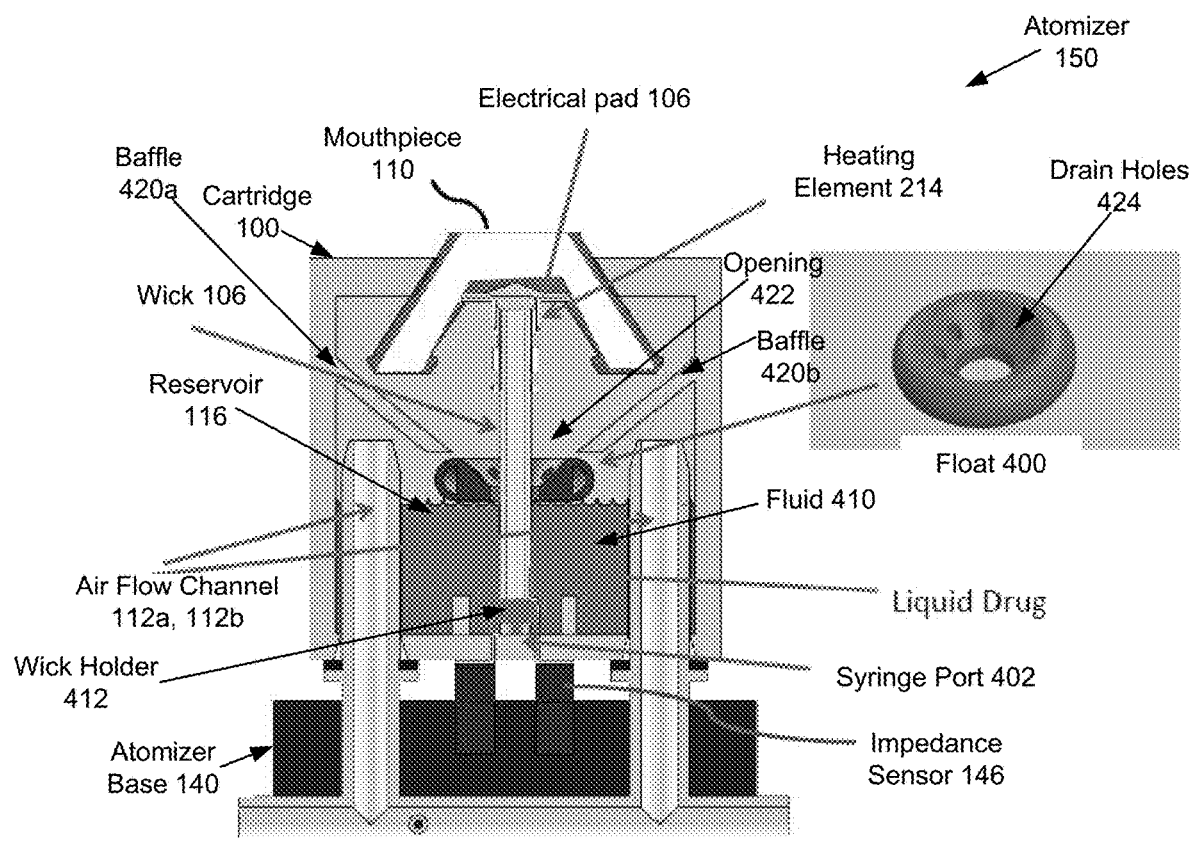
FIG. 4 illustrates a schematic block diagram of another embodiment of the atomizer.
Figure 5:
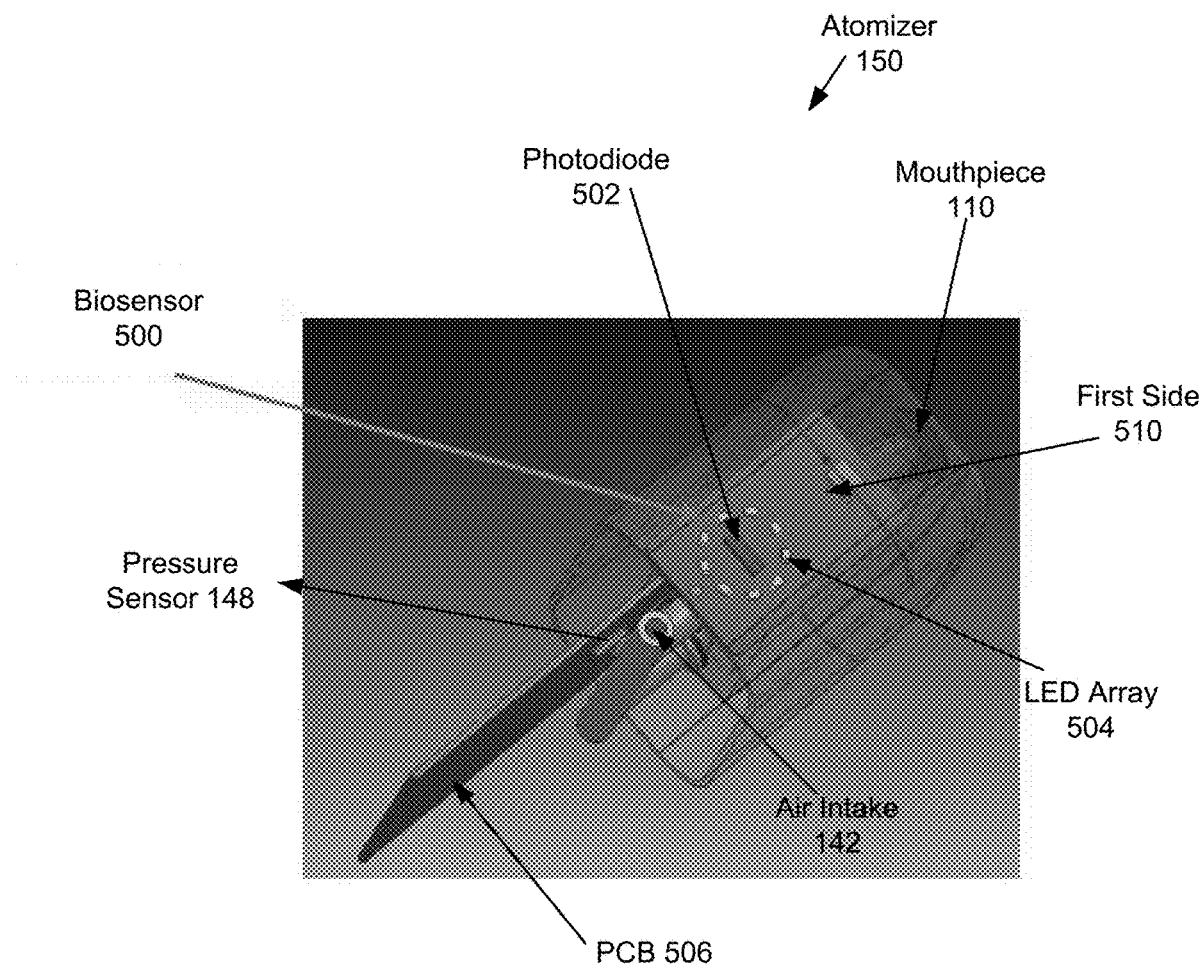
FIG. 5 illustrates a perspective view of an embodiment of an atomizer including a biosensor.
Figure 6:
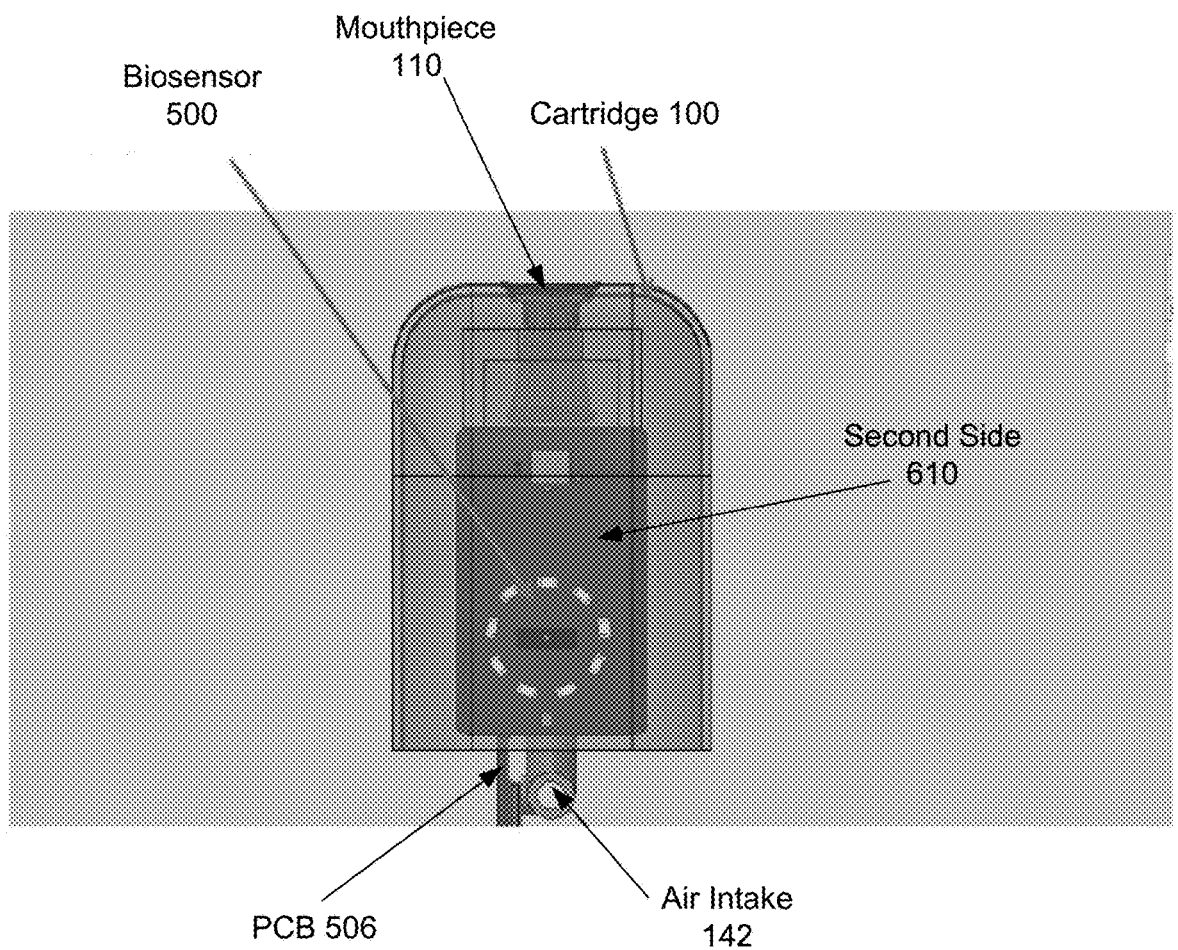
FIG. 6 illustrates a perspective view of an embodiment of an atomizer including a biosensor.

FIG. 3 illustrates a schematic block diagram of an embodiment of the atomizer 150 including a respiration activation system. In one aspect, the respiration activation system includes a pressure sensor 148 and heating system 104. The pressure sensor 148 measures air flow through the air passageway 144 between the air flow channels 112a, 112b and the air intake 142. From the measurements, periods of inhalation and exhalation may be determined. For example, the pressure sensor 148 may measure a first, positive pressure during inhalation and a second, negative pressure during exhalation. For the inhalation period, the heating system 104 is controlled to generate an increased amount of vapor at the mouthpiece. For the exhalation period, the heating system 104 is controlled to decrease vapor at the mouthpiece.

The heating system 104 heats the fluid in the wick 106 producing gaseous vapors including atomized particles. The vapor flows between the sets of baffles and is channeled into one or more openings in the mouthpiece 110. The upper set of baffles 118a,b help to prevent large droplets or fluid from entering the mouthpiece 110. The lower set of baffles 118c,d help prevent leakage of the fluid into the passageway. The upper set and lower set of baffles form an air flow chamber 130 within the cartridge 100. The air flow chamber 130 enhances turbulence and mixing of the vapor and air. The gas also cools as it circulates in the airflow chamber 130 before escaping into the mouthpiece. The air flow chamber 130 increases airflow turbulence of the atomized air inside the cartridge by using outside airflow and blocking an air path to the mouthpiece. This enhances mixing of the vapor and provides enhanced shielding to prevent accidental leakage of fluid from the cartridge 100.

In another aspect, the atomizer 150 is configured to measure a fluid level or amount and control operation of the device in response to the fluid level. For example, when the fluid level falls beneath a predetermined threshold, the heating system 104 is deactivated. The deactivation prevents operation of the atomizer 150 with little to no fluid. A signal light or other display may indicate that the cartridge 100 needs to be replaced. In another aspect, when the cartridge 100 is inserted into the atomizer base 140, a fluid level is determined. When the fluid level is not within a predetermined range expected for the cartridge 100, the atomizer 150 is not activated. This check helps prevent faulty cartridges or unauthorized cartridges from being used with the atomizer base 140.

The fluid level may be measured using one or more methods. In one embodiment, the cartridge 100 includes one or more electrical pads 106*a,b* configured to electrically couple with the atomizer base 140. The electrical pads 106*a,b* are further configured to assist in measurement of an impendence of the wick 106. The measured impedance may be an ohmic resistance and/or reactance, e.g., a capacitance, inductance and/or resistance of the wick 106. For example, the electrical pads 106*a,b* may be electrically coupled to a heating element 214 situated around the wick 106. In a heating mode, the heating system 104 activates the heating element 214 to heat the wick 106.

In a measurement mode, an impedance sensor 146 measures an impedance of the wick 106. The impedance is used to determine whether to activate operation of the heating system 104. The impedance of the wick 106 may also be measured to determine a fluid level at insertion of the cartridge 100 and/or in between uses of the atomizer 150. The impedance of the wick 106 will vary according to an amount of fluid in the cartridge 100, and so an amount of the fluid in the cartridge 100 may be estimated based on the impedance. The user may be alerted to change the cartridge 100 when the fluid level is low. The cartridge 100 may be configured to switch between a heating mode and impedance measuring mode using the same electrical pads 106 and heating element 214 for both the heating system 104 and impedance sensor 146.

The bottom of the cartridge 100 may include a one-time seal to prevent foreign particles from entering the cartridge during manufacturing and storage. When the cartridge 100 is inserted into the atomizer base 140, the atomizer 140 senses the cartridge 100 through the electrical pads 106a,b. The atomizer 150 automatically measures the fluid level. When the fluid level is not within a predetermined range expected for a full cartridge 100, the atomizer 150 is not activated. This check helps prevent faulty cartridges or unauthorized cartridges from being used with the atomizer base 140. In addition, the cartridge 100 may not be intended to be removed until treatment is complete. The check prevents removal of the cartridge after use and then reinsertion of the same cartridge 100.

The atomizer 150 is thus configured to track respiration and release the gaseous atomized drugs into the deep lung areas during an inhalation period. The atomizer 150 may also obtain a fluid level by measuring an impedance of the wick 106. The cartridge 100 is configured to enhance airflow between the sets of baffles 118. The baffles 118 enhance air recirculation and mixing of hot atomized gases containing the fluid to allow some cooling effect to the turbulent vapors prior to inhalation. The baffles 118 also isolate the fluid from the mouthpiece 110 to help prevent un-intended leakage to the user.

FIG. 4 illustrates a schematic block diagram of another embodiment of the atomizer 150. The atomizer 150 includes a wick 106 that extends from a top portion of the cartridge 100 to a bottom portion of the cartridge 100. A wick holder 412 is configured at the bottom portion of the cartridge 100 to secure the wick 106. The heating element 214 is configured at a top portion of the wick 106 and is coupled to the electrical pad 106. The impedance sensor 146 is also electrically coupled to the electrical pad 106. The impedance sensor 146 measures the impedance of the wick 106. The wick 106 absorbs fluid 410 from the reservoir 116. The impedance of the wick 106 changes as the fluid is absorbed. When the fluid lowers, the wick 106 absorbs less fluid and the impedance of the wick 106 is altered.

In one aspect, the cartridge 100 includes one or more baffles 420*a*, 420*b* slanting downward into the reservoir 116. The baffles 420*a*, 420*b* form an opening 422. To prevent fluid 410 from freely flowing into the upper portion of the reservoir 116, a float 400 is positioned within the reservoir 116 across the opening 422. The float 400 is configured with a diameter that is equal to or greater than the width of the opening 422. The float 400 may comprise a material that floats on the fluid 410 or otherwise is positioned between the fluid 410 and the opening 422.

The float 400 includes one or more float holes 424. Any fluid 410, vapor or large droplets that flow into the upper portion of the reservoir 116 over the baffles 420, may flow back into the lower portion of the reservoir through the float holes 424. The float 410 helps to prevent a free flow of the fluid 410 through the opening 422.

In use, the atomizer 150 detects an inhalation period using the pressure sensor 148 to determine whether or not to active the treatment cycle. When a treatment cycle is initiated, the heating element 214 is activated via the electrical pads 106. This heating cycle is activated via a pulse width modulated power circuit until a predetermined or desired temperature is reached or maximum heating time window is reached. During the initial dosing, the heating element 214 will break down the heat soluble material in the wick 106 and break the seal 205 to allow the intended drug to begin mixing and intermixing into the wick material while producing atomized vapors. In one embodiment, the heater element temperature of the cartridge 100 is intended to reach a maximum temperature of approximately 220 degrees Celsius internal temperature for safety reasons. A different maximum temperature or range of temperatures may be desired for different implementations and drugs.

The atomizer 150 thus assists a patient receiving respiratory treatments with enhanced means to track the inhale/exhale breathing cycles and deliver atomized vapor in the deep lung areas. The atomizer 150 also provides a disposable cartridge containing a predetermined amount of fluid or medicine along with a smart delivery device which can monitor fluid levels.

FIG. 5 illustrates a perspective view of an embodiment of an atomizer 150 including a biosensor 500. The biosensor 500 may be integrated at first side 510 of the atomizer 150 and includes a photodiode 502 and LED array 504 as part of a photoplethysmography (PPG) based optical sensor that may be configured to continuously or periodically measure a patient's vitals, such as heart rate, pulse, blood oxygen levels, blood gases such as Nitric Oxide, and specific drug concentrations, etc.

FIG. 6 illustrates a perspective view of an embodiment of an atomizer 150 including a biosensor 500. The biosensor 500 may be integrated at a second top side 610 of the atomizer 150 and includes a photodiode 502 and LED array 504 for performing PPG analysis as described in more detail herein.

The biosensor 500 is configured to measure vital signs of a user of the atomizer 150 and may also measure substances in a user's blood vessels and/or tissue. This biosensor 500 data helps to determine a level of efficacy of the treatment and an adverse reaction to the treatment. The pressure sensor 148 may be used with the biosensor 500 to measure air temperature of the airways and the flow of the inhale/exhale breathing cycle to time output of the vapors during treatment. This monitoring process can provide very useful information for the intended treatment and ensure the treatment was successful.

The biosensor 500 data may be stored on a memory on a printed circuit board PCB 506. The PCB 506 may also include a wireless transmitter that is configured to communicate with a healthcare facility network or other LAN, MAN or WAN that stores and maintains an electronic medical record of the patient. When a cartridge 100 is inserted into the atomizer 150, the user can place a finger on the biosensor 500. The biosensor 500 may be configured to automatically detect the presence of the finger and initiate an inhalation treatment. The patient's vitals are measured, and the respiration cycle is determined. The heating system is activated in response to the respiration cycle to deliver vaporized medicine at the mouthpiece during an inhalation period and decrease output of the vaporized medicine at the mouthpiece during exhalation. The biosensor 500 measures vital signs and/or substances in the blood flow or tissue of the user to assist in determining a level of efficacy of the treatment or a possible adverse reaction to the treatment.

Figure 7:
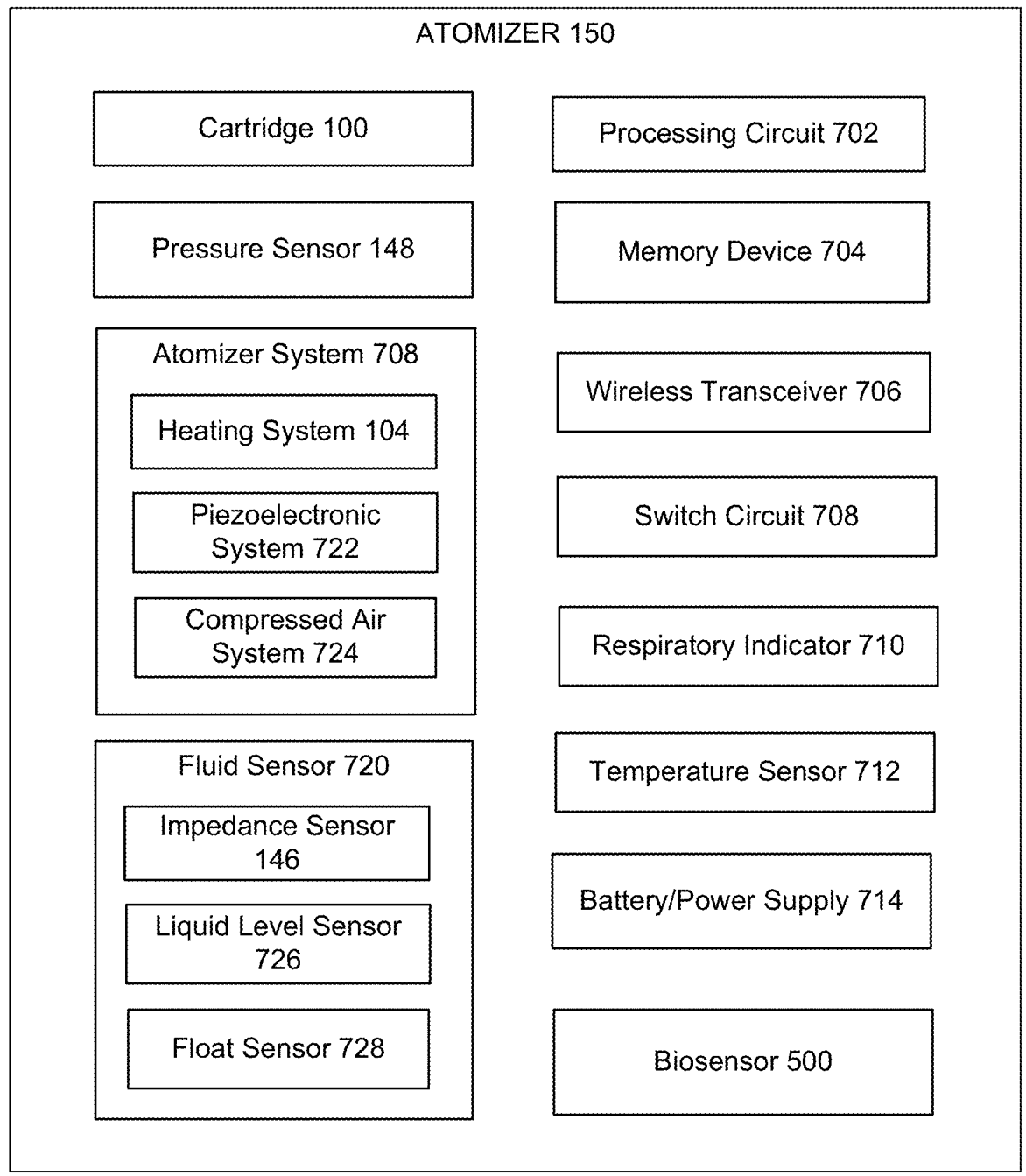
FIG. 7 illustrates a schematic block diagram of an exemplary embodiment of the atomizer with a cartridge.

FIG. 7 illustrates a schematic block diagram of an exemplary embodiment of the atomizer 150 with a cartridge 100. The cartridge 100 may be replaceable or refillable. In an embodiment, the atomizer 150 includes a processing circuit 702, a memory 704 and wireless transceiver 706. The atomizer 150 further includes a pressure sensor 148 configured to measure inhalation and exhalation periods. Though a pressure sensor 148 is described herein, the biosensor 500 or other respiratory indicator 710 may be used to determine inhalation and exhalation periods and/or respiration rate of a user. The processing circuit 702 is configured to perform one or more functions described herein. For example, the processing circuit 702 may control the atomizer system 708 and fluid sensor 720 and switch circuit 708 to switch between the atomizer system 708 and fluid sensor 720 if needed. The atomizer system 708 is configured to atomize fluid in the cartridge 100 to vapor. Though a heating system 100 is described herein, the atomizer system 708 may alternatively include a piezoelectronic system 724 or compressed air system 726 or other system configured to atomize fluid in the cartridge 100 to vapor.

The fluid sensor 720 is configured to detect a fluid amount or level in the cartridge 100. The fluid sensor 720 may include the impedance sensor 146 described herein. Alternatively, the fluid sensor 720 may be implemented using a liquid level sensor 726 or float sensor 728 or other type of fluid sensor configured to detect the fluid amount or level in the cartridge 100.

The atomizer 150 may further include the biosensor 500, a temperature sensor 712 and a battery or other power supply 714.

Figure 8:
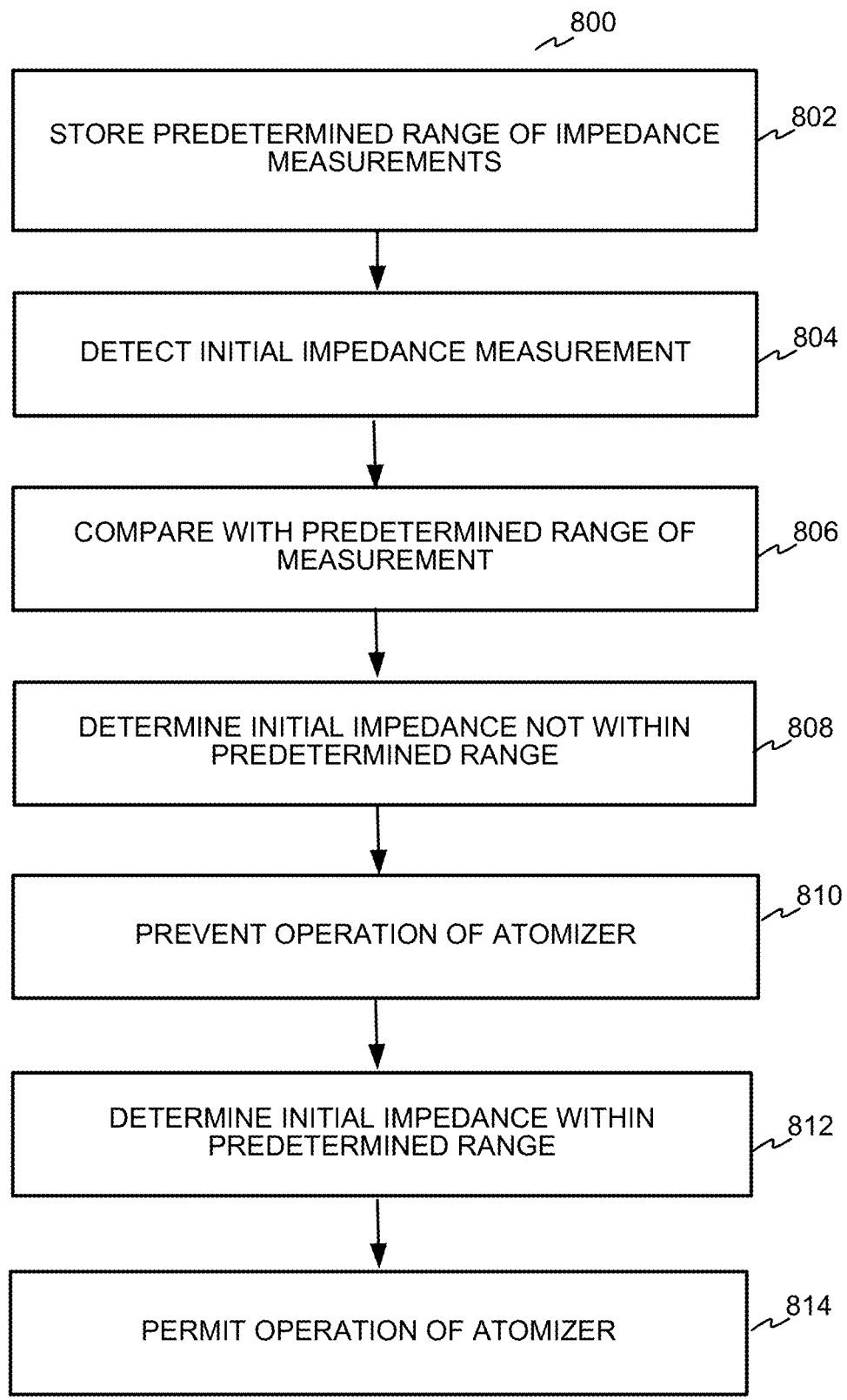
FIG. 8 illustrates a logical flow diagram of an embodiment of a method of operation of the atomizer.

FIG. 8 illustrates a logical flow diagram of an embodiment of a method 800 of operation of the atomizer 150. During manufacture or software updates, a predetermined range of an initial impedance measurement is stored in a memory of the atomizer 150 at 802. The initial impedance measurement may include a combination of one or more of: an ohmic resistance, inductance or capacitance. The predetermined range is determined based on measurements of the wick's impedance upon activation of a cartridge with a known dosage of medication or other fluid. For example, impedance measurements are obtained from a sample set of cartridges with a desired amount of fluid prior to a first atomization. A range of the initial impedance measurements within a tolerance is stored in a memory of the cartridge 100.

In use, an impedance sensor 146 measures an initial impedance of the wick 106 prior to a first atomization at 804. The initial impedance is used to determine whether to activate operation of the heating system 104. The initial impedance of the wick may automatically be measured at insertion of the cartridge 100 in the atomizer 150. The impedance measurement is then compared with the predetermined range of initial impedance measurements at 806. The initial impedance is determined to not be within the predetermined range at 808. The atomizer 150 then prevents heating of the heating element in a first atomization mode or other operation of the atomizer 150 at 810. This check helps prevent faulty cartridges or unauthorized cartridges from being used with the atomizer base 140. In addition, the cartridge 100 may not be intended to be removed until treatment is complete. The check prevents removal of the cartridge after use and then reinsertion of the same cartridge 100.

The initial impedance is determined to be within the predetermined range at 812. The atomizer 150 then permits or activates operation of the heating system or other operations of the atomizer 150 at 814. For example, the atomizer 150 may permit or initiate a first atomization mode of the atomizer 150.

Figure 9:
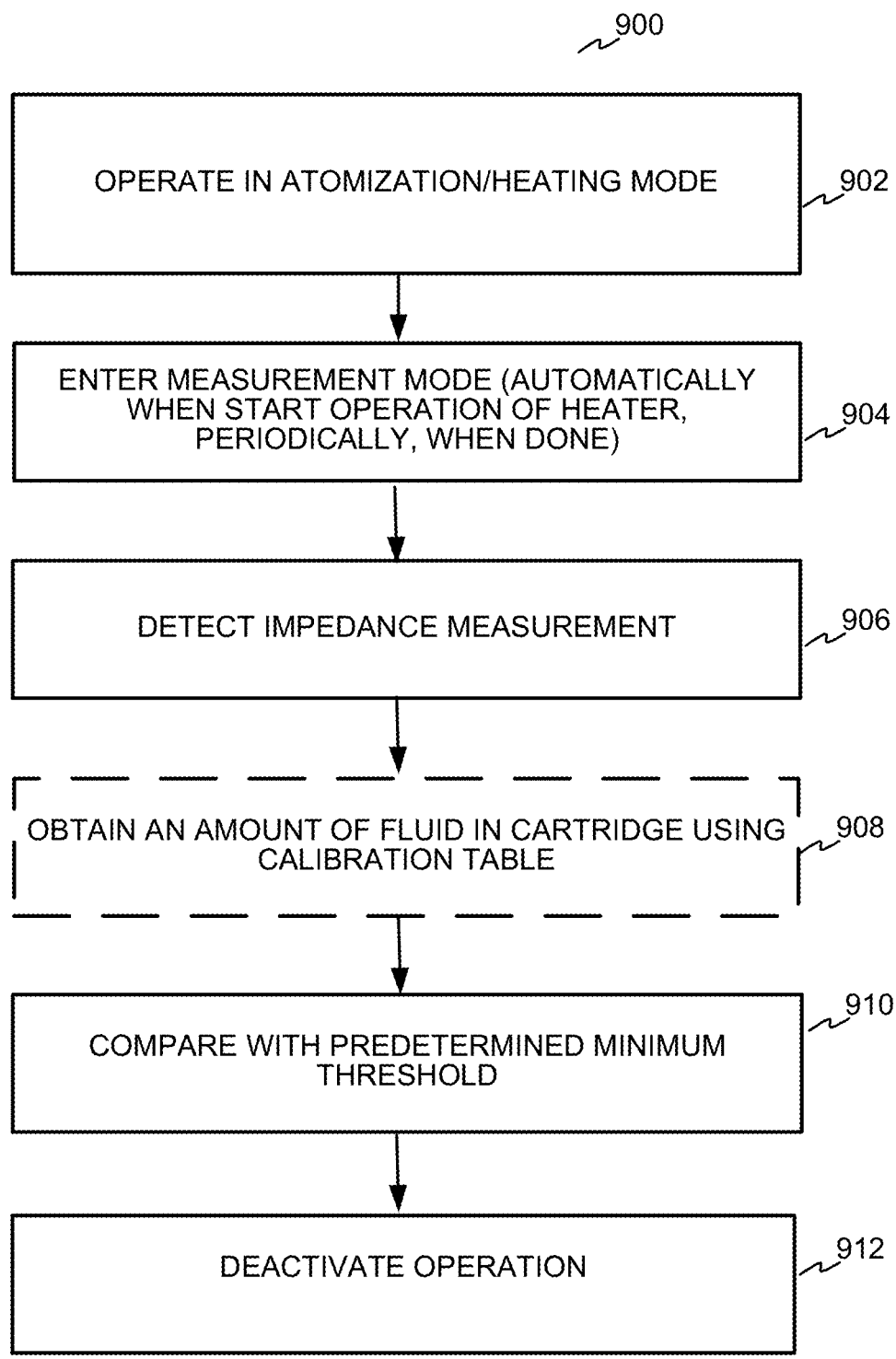
FIG. 9 illustrates a logical flow diagram of another embodiment of a method 900 of operation of the atomizer.

FIG. 9 illustrates a logical flow diagram of another embodiment of a method 900 of operation of the atomizer 150. After activation of the atomizer 150, the heating system 104 operates in a heating mode to heat the wick 106 to generate vapor at 902. The atomizer 150 may switch to measurement mode at 904. For example, the atomizer 150 may periodically enter a measurement mode during treatment. The atomizer 150 may also enter a measurement mode during a detected exhalation period. The atomizer 150 may further enter a measurement mode after a predetermined time without detection of inhalation or exhalation. An impedance measurement of the wick 106 is detected at 906.

Optionally, the impedance measurement may be used to obtain a level or amount of fluid in the cartridge 100. For example, the impedance measurements are associated with corresponding fluid levels/amounts in the cartridge 100 and stored in a calibration table in a memory of the atomizer 150. The fluid level may then be displayed or indicated using a light emitter diode (LED).

The impedance measurement is compared with a predetermined minimum threshold at 910. When the impedance measurement is below the minimum threshold, the atomizer 150 deactivates operation of the heating element 214 at 912. The low fluid level may then be displayed or indicated using a light emitter diode (LED). A user may thus determine when the fluid is low, and the cartridge 100 needs replacement.

Figure 10:
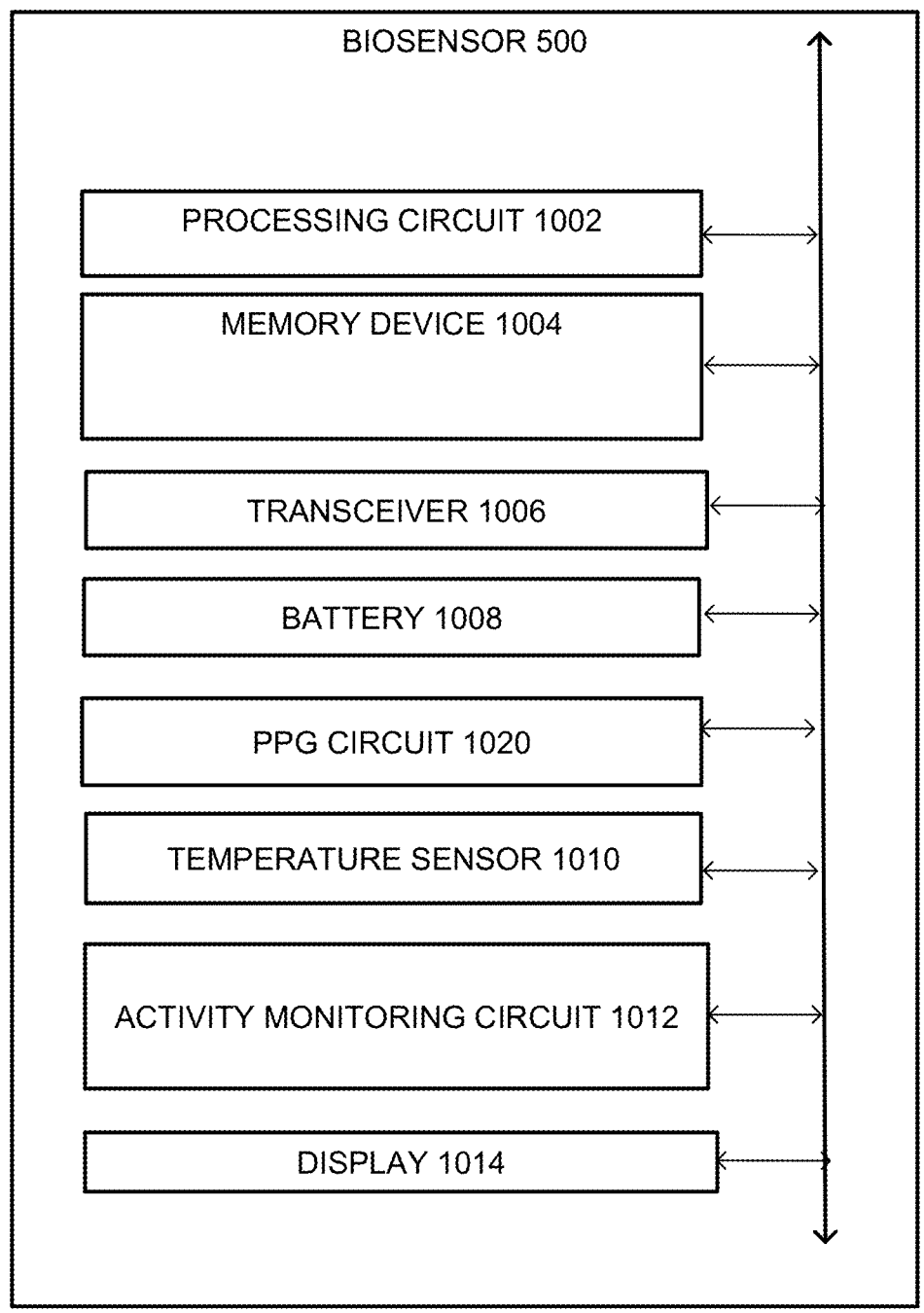
FIG. 10 illustrates a schematic block diagram of an exemplary embodiment of a biosensor.

FIG. 10 illustrates a schematic block diagram of an exemplary embodiment of a biosensor 500. In an embodiment, the biosensor 500 includes a photoplethysmography (PPG) circuit 1020 that may be configured to continuously or periodically measure a patient's vitals, such as heart rate, pulse, blood oxygen levels, blood gases such as Nitric Oxide, and specific drug concentrations, etc. The patient's vitals are thus monitored by the biosensor 500 without manual intervention or additional instruments. The biosensor 500 may be used to track progress throughout the patient treatment cycle and provide medical alerts to notify when vitals are critical.

The biosensor 500 may be integrated with the atomizer 150 or may be external to the atomizer 150 and in wireless communication with the atomizer 150. When located externally, the biosensor 500 may include a separate processing circuit 1002, memory device 1004, transceiver 1006 and battery 1008. When integrated with the atomizer 150, the biosensor 500 may include separate components or may share or utilize the processing circuit 702, memory 704, battery/power supply 714, transceiver 706 or other components of the atomizer 500. The biosensor 500 may include a thermometer or other temperature sensor 1010, and activity monitoring circuit 1012.

The processing circuit 1002 is communicatively coupled to the memory device 1004, transceiver 1006 and PPG Circuit 1020. For example, the memory device 1004 includes one or more non-transitory processor readable memories that store instructions which when executed by the processing circuit 1002, causes the processing circuit 1002 to perform one or more functions described herein. The memory device 1004 may also include an EEPROM to store the patient identification. The memory device 1004 may also store a medical record or portion of the treatment data of the patient or one or more measurements of the vitals by the biosensor 500. The processing circuit 1002 may be collocated with the PPG circuit 1020 in a same physical encasement or located separately in a different physical encasement or located remotely.

The transceiver 1006 may be a Bluetooth enabled (BLE) wireless transceiver or may utilize another standard or proprietary protocol, such as IEEE 802.11ah, Zigbee, IEEE 802.15-11 etc. In one or more aspects, the transceiver 1006 operates in one or more other protocols, such as near field communication, short range radio frequency, RFID, infrared link, WLAN (such as an IEEE 802.11 standard protocol) or other short range wireless communication protocol. In one or more aspects, the transceiver 1006 may include an IR wireless transceiver. The transceiver 1006 may also include or alternatively include a wireless transceiver for communicating over a cellular network or other type of wireless network. The biosensor 500 may also include a USB port for a wired connection to one or more other devices.

The photoplethysmography (PPG) circuit 1020 includes for example an infrared (IR) pulse oximeter configured to track a pulse rate and oxygen levels in the blood of patient. The PPG circuit may also be configured to monitor blood pressure using IR reflected light.

In an embodiment, the biosensor 500 is battery operated and includes a battery 1008. To help lower power consumption, in an embodiment, the biosensor 500 includes the activity monitoring circuit 1012 for monitoring activity. For example, the activity monitoring circuit 1012 may include a three-axis accelerometer that measures a position of the patient's head and motion from normal activities. When a patient is still for a predetermined time period, such as during sleep, the activity monitoring circuit 1012 detects little to no movement and signals the biosensor 500 and/or atomizer 150 to enter into a rest mode. In the rest mode, the biosensor 500 and/or atomizer 150 halts non-essential processing functions. When the activity monitoring circuit 1012 detects movement for another predetermined time period, the activity monitoring circuit 1012 signals the biosensor 500 and/or atomizer 150 to exit rest mode and resume monitoring. This activity monitoring feature helps to save power and extend battery life.

The biosensor 500 may also include a display 1014 configured to display biosensor 500 data or operational data of the atomizer 150, such as fluid level.

Figure 11:
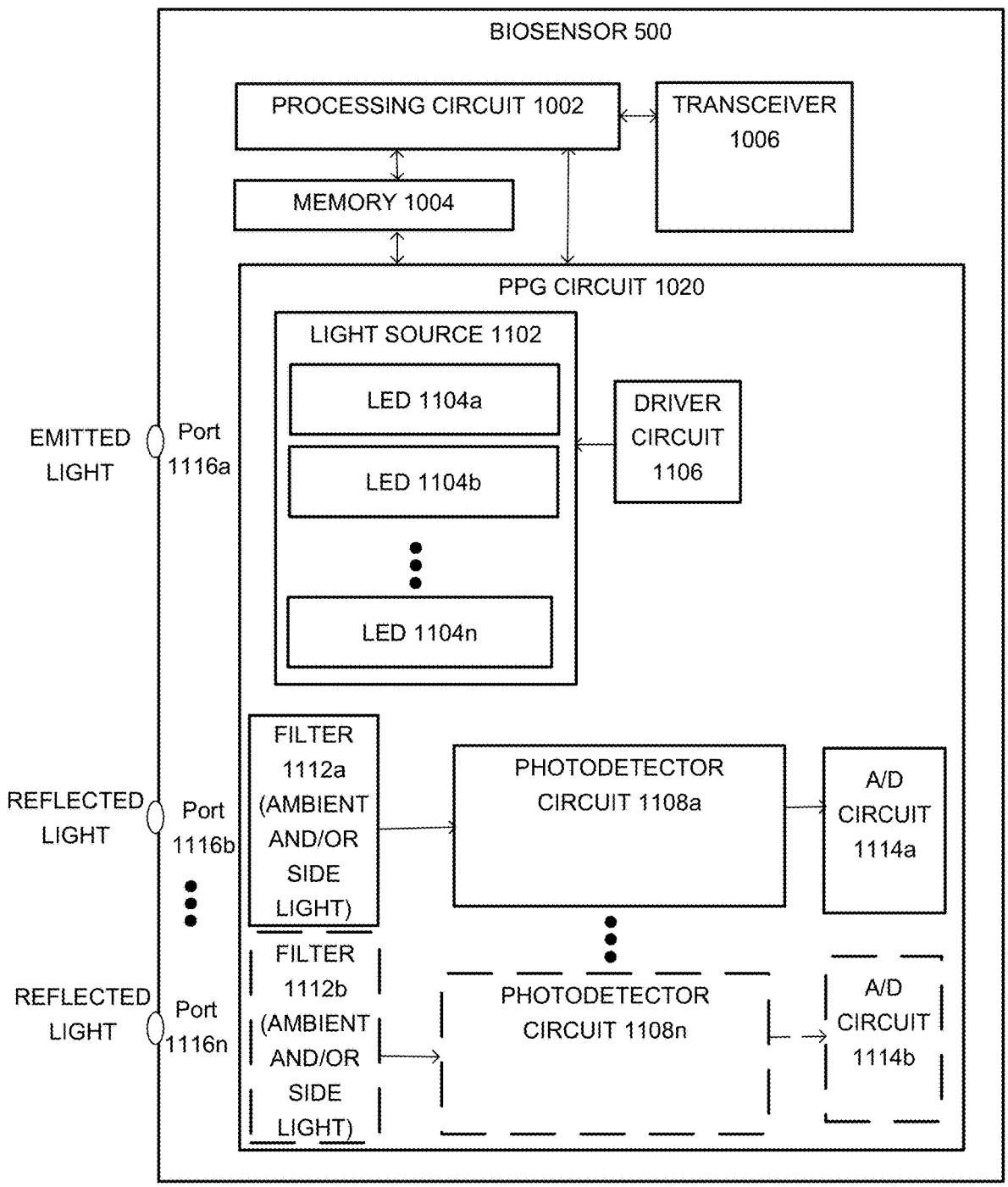
FIG. 11 illustrates a schematic block diagram of an exemplary embodiment of the biosensor 500 illustrating the PPG Circuit 1020 in more detail.

FIG. 11 illustrates a schematic block diagram of an exemplary embodiment of the biosensor 500 illustrating the PPG Circuit 1020 in more detail. The PPG circuit 1020 is configured to detect one or more substances in pulsating arterial blood flow. The PPG Circuit 1020 includes a light source 1102 having a plurality of light sources or LEDs 1104 for emitting one or more of infrared (IR) light, (UV) light, near IR light and/or visible light. For example, the PPG Circuit 1020 may include a first LED 1104a that emits visible light and a second LED 1104b that emits an IR light and a third LED 1104n that emits light a UV light, etc.

In an embodiment, a driver circuit 1106 is configured to drive the one or more LEDs 1104a-n separately to generate a broad spectrum of light directed at living tissue to perform various non-invasive measurement techniques, as described further herein. A light collimator, such as a prism, may be used to align a direction of the light parallel to the living tissue that is emitted from the LEDs 1104. The biosensor 500 is thus configured to emit a broad spectrum of light in one or predetermined plurality of frequencies of light in one or more of the visible, UV or IR electromagnetic spectrum. The light is emitted through one or more ports 1116a or other interfaces directed at living tissue.

The PPG circuit 1020 further includes one or more photodetector circuits 1108a-n. For example, a first photodetector circuit 1108 may be configured to detect visible light and the second photodetector circuit 1108 may be configured to detect IR light and a third photodetector 1108n configured to detect UV light. Alternatively, a single photodetector may be implemented to detect light over multiple spectrums. The PPG circuit 1030 may also include one or more filters, such as filter 1112a and filter 1112b, configured to filter ambient light and/or scattered light. For example, the filters 1112 may only pass light reflected at an approximately perpendicular angle from the skin of the patient and filter scattered light from other angles. The photodetector circuits 1108 may include a spectrometer or other type of circuit that detects an intensity of light as a function of wavelength or of frequency. For example, the PPG Circuit 1020 may include a Digital UV Index/IR/Visible Light Sensor.

The first photodetector circuit 1108a and the second photodetector circuit 1108b are coupled to a first A/D circuit 1114a and a second A/D circuit 1114b. Alternatively, a single A/D circuit 1114 may be coupled to each of the photodetector circuits 1108 or integrated with the photodetector circuits 1108. The PPG circuit 1020 is thus configured to obtain a spectral response at one or more predetermined frequencies or across a broad spectrum. The biosensor 500 may then perform an analysis of spectral responses as described in more detail herein.

Figure 12:
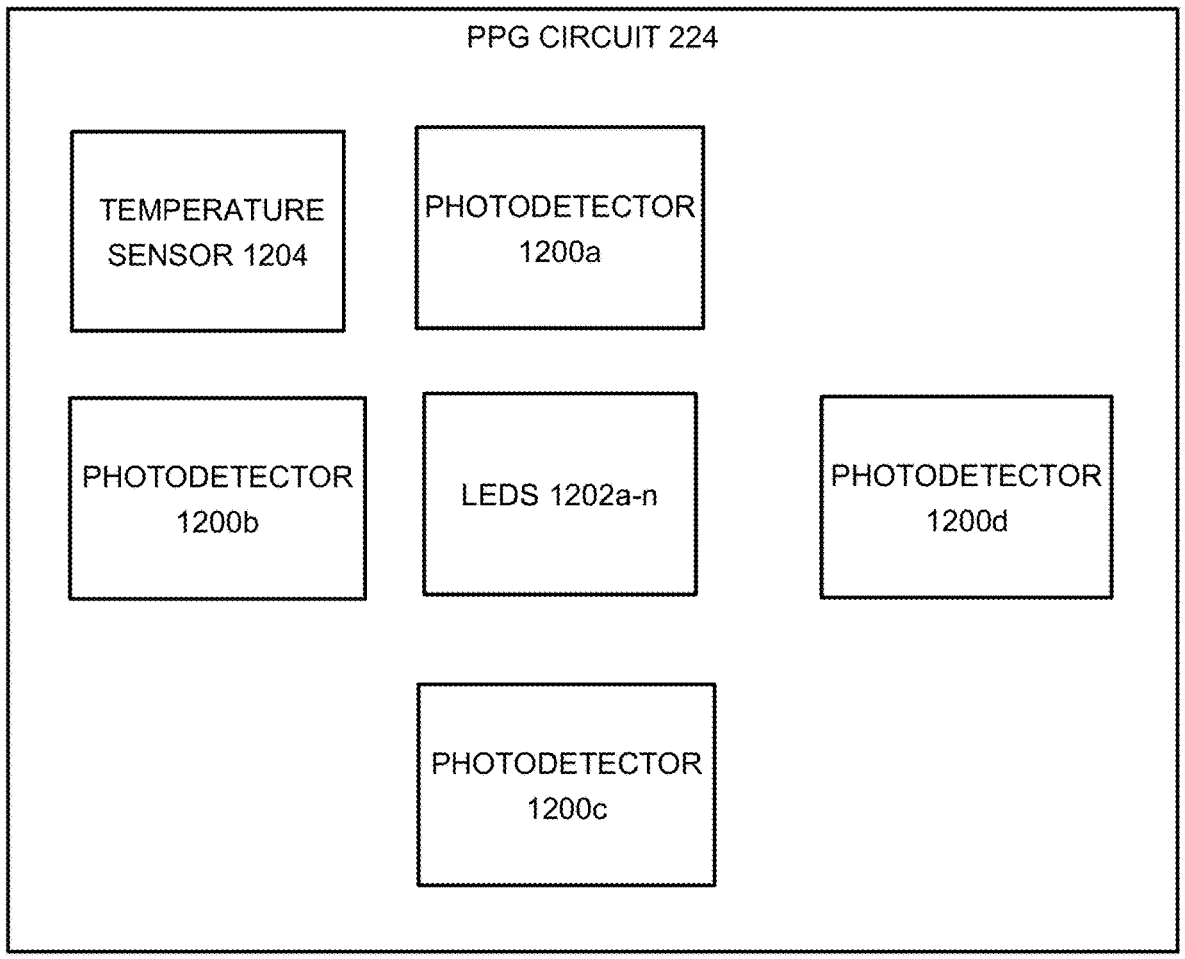
FIG. 12 illustrates a schematic block diagram of an embodiment of the PPG circuit with a plurality of photodetectors.

FIG. 12 illustrates a schematic block diagram of an embodiment of the PPG circuit 1020 with a plurality of photodetectors 1200a, 1200b, 1200c, 1200d. In one aspect, the plurality of photodetectors 1200 are situated in different physical positions and orientations on the atomizer 150 in the biosensor 500. For example, at least four photodetectors 1200 are situated in the biosensor 500 in four different physical positions in a North-South and East-West orientation or polarity. The output signals of the plurality of photodetectors 1200 are coupled in parallel to an amplifier and A/D circuit 1114. The light signals detected by each of the photodetectors 1200 through an aperture in the biosensor 500 are added and amplified to generate a single spectral response. The spectral response is thus more robust and less affected by motion artifacts and movement of the biosensor 500. The LEDs 1202a-n may be situated centrally to the physical position of the plurality of photodetectors. The temperature sensor 1204 may also be physically situated near the PPG circuit 1020 to detect temperature through an aperture.

Using the PPG circuit, the biosensor 500 is configured to detect and/or store biosensor 500 data of a patient. For example, the biosensor 500 may detect nicotine indicators or level of nitrates and predict cardiovascular risk precursors. The biosensor 500 may detect nicotine response, vascular health, cardiovascular sensor, cytochrome P450 proteins (e.g. one or more liver enzymes or reactions), digestion phase 1 and 2, blood oxygen levels, pulse rate, blood pressure. The biosensor 500 may even be configured to detect proteins or other elements or compounds associated with cancer. The biosensor 500 may also function as a pulse oximeter to determine pulse and oxygen levels. The biosensor 500 may also detect blood pressure, peripheral oxygen (SpO2) saturation amounts, various electrolytes and many common blood analytic levels, such as bilirubin amount and sodium and potassium. For example, the biosensor 500 may detect sodium NACL concentration levels in vivo in the arterial blood flow to determine dehydration.

In use, the biosensor 500 performs spectroscopy to detect blood analytes and arterial flow. In one aspect, the biosensor 500 analyzes reflected visible or IR light to determine a spectral response such as, the resonance absorption peaks of the reflected visible or IR light. The spectral response includes spectral lines that illustrate an intensity or power or energy at a frequency or wavelength in a spectral region of the reflected light.

The ratio of the resonance absorption peaks from two different frequencies can be calculated based on the Beer-Lambert law to determine various levels of substances in the arterial blood flow. The spectral response of a substance or substances is determined, so the molar attenuation coefficient $\varepsilon$ can be determined. Measurements of decadic attenuation coefficient $\mu_{10}$ are made at a first wavelength $\lambda_1$ and at a second wavelength $\lambda_2$ in order to correct for possible interferences. The concentration c may then be determined from the Beer-Lambert Law as:

$$c = \frac{\mu_{10}(\lambda)}{\varepsilon(\lambda)}.$$

According to the Beer-Lambert law, light intensity will decrease logarithmically with path length l (such as through an artery of length l). Assuming then an initial intensity $I_{in}$ of light is passed through a path length l, a concentration $C_g$ of a substance may be determined using the following equations:

At the first wavelength $\lambda 1, I_1 = I_{in1} * 10^{-(\alpha_{g1} C_{gw} + \alpha_{w1} C_w) * l}$ At the second wavelength $\lambda 2, I_2 = I_{in2} * 10^{-(\alpha_{g2} C_{gw} + \alpha_{w2} C_w) * l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in water at $\lambda_1$
$\alpha_{g2}$ is the absorption coefficient of the substance in water at $\lambda_2$
$\alpha_{w1}$ is the absorption coefficient of water at $\lambda_1$
$\alpha_{w2}$ is the absorption coefficient of water at $\lambda_2$
$C_{gw}$ is the concentration of the substance and water
$C_w$ is the concentration of water
Then letting R equal:

$$R = \frac{\log 10\left(\frac{I_1}{I_{in1}}\right)}{\log 10\left(\frac{I_2}{I_{in2}}\right)}$$

The concentration of the substance Cg may then be equal to:

$$Cg = \frac{Cgw}{Cgw + Cw} = \frac{\alpha_{w2} R - \alpha_{w1}}{(\alpha_{w2} - \alpha_{gw2}) * R - (\alpha_{w1} - \alpha_{gw1})}$$

The biosensor 500 may thus determine the concentration of various substances using spectroscopy at two different wavelengths using Beer-Lambert principles. In an embodiment, a first wavelength is in the IR range from approximately 700 nanometers (frequency 430 THz) to approximately 1 mm (300 GHz) and a second wavelength in the visible light range.

The biosensor 500 may also function as a pulse oximeter using similar principles under Beer-Lambert law to determine pulse and oxygen levels. For example, the first wavelength is approximately 940 nm and the second wavelength is approximately 640 nm when determining pulse and oxygen levels.

The biosensor 500 may also detect other substances using the spectral responses at predetermined wavelengths using the principles of the Beer-Lambert law. For example, the spectral response of the reflected light is analyzed at incremental wavelengths, e.g., at 1 nm or 1.5 nm or 2 nm, across a range of wavelengths, e.g. from 350 nm to 2500 nm. In another embodiment, the spectral response of the reflected light is analyzed for a plurality of predetermined wavelengths.

Figure 13:
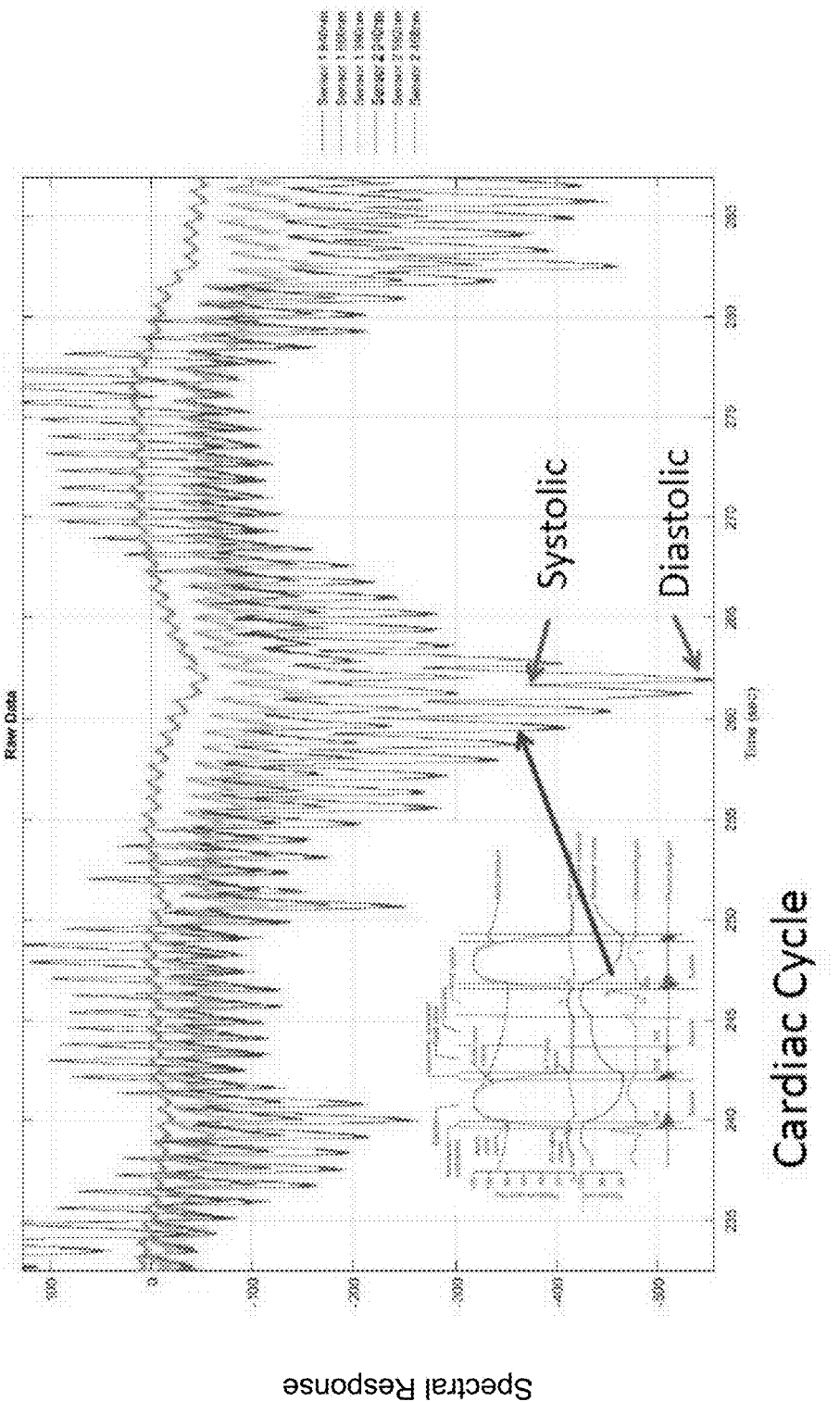
FIG. 13 illustrates a schematic diagram of a graph of actual clinical data obtained from an example biosensor using PPG techniques at a plurality of wavelengths.

FIG. 13 illustrates a schematic diagram of a graph of actual clinical data obtained from an example biosensor 500 using PPG techniques at a plurality of wavelengths. The biosensor 500 emits light having a plurality of wavelengths during a measurement period. The light at each wavelength (or range of wavelengths) may be emitted concurrently or sequentially. The intensity of the reflected light at each of the wavelengths (or range of wavelengths) is detected and the spectral response is measured over the measurement period. The spectral response for the plurality of wavelengths obtained using the biosensor 500 in clinical trials is shown in FIG. 13. In this clinical trial, two exemplary biosensors 500 were attached to two separate fingertips of a patient to obtain the illustrated spectral responses. The first biosensor 500 obtained the spectral response for a wavelength at 940 nm, a wavelength at 660 nm and a wavelength at 390 nm. The second biosensor 500 obtained the spectral response for a wavelength at 940 nm, a wavelength at 592 nm and a wavelength at 468 nm. Though two biosensors were used in this example, one biosensor 500 may be configured to determine the spectral responses at each wavelength.

In one aspect, the spectral response of each wavelength may be aligned based on the systolic and diastolic points in their spectral responses. This alignment is useful to associate each spectral response with a particular stage or phase of the pulse-induced local pressure wave within the blood vessel (which may mimic the cardiac cycle and thus include systolic and diastolic stages and sub-stages thereof). This temporal alignment helps to determine the absorption measurements acquired near a systolic point in time of the cardiac cycle and near the diastolic point in time of the cardiac cycle associated with the local pressure wave within the patient's blood vessels. This measured local pulse timing information may be useful for properly interpreting the absorption measurements in order to determine the relative contributions of the AC and DC components measured by the biosensor 500. So for one or more wavelengths, the systolic points and diastolic points in the spectral response are determined. These systolic points and diastolic points for the one or more wavelengths may then be aligned as a method to discern relatively concurrent responses across the one or more wavelengths.

In another embodiment, the the systolic points and diastolic points in the absorbance measurements are temporally correlated to the pulse-driven pressure wave within the arterial blood vessels—which may differ from the cardiac cycle. In another embodiment, the biosensor 500 may concurrently measure the intensity reflected at each of the plurality of wavelengths. Since the measurements are concurrent, no alignment of the spectral responses of the plurality of wavelengths may be necessary.

Figure 14:
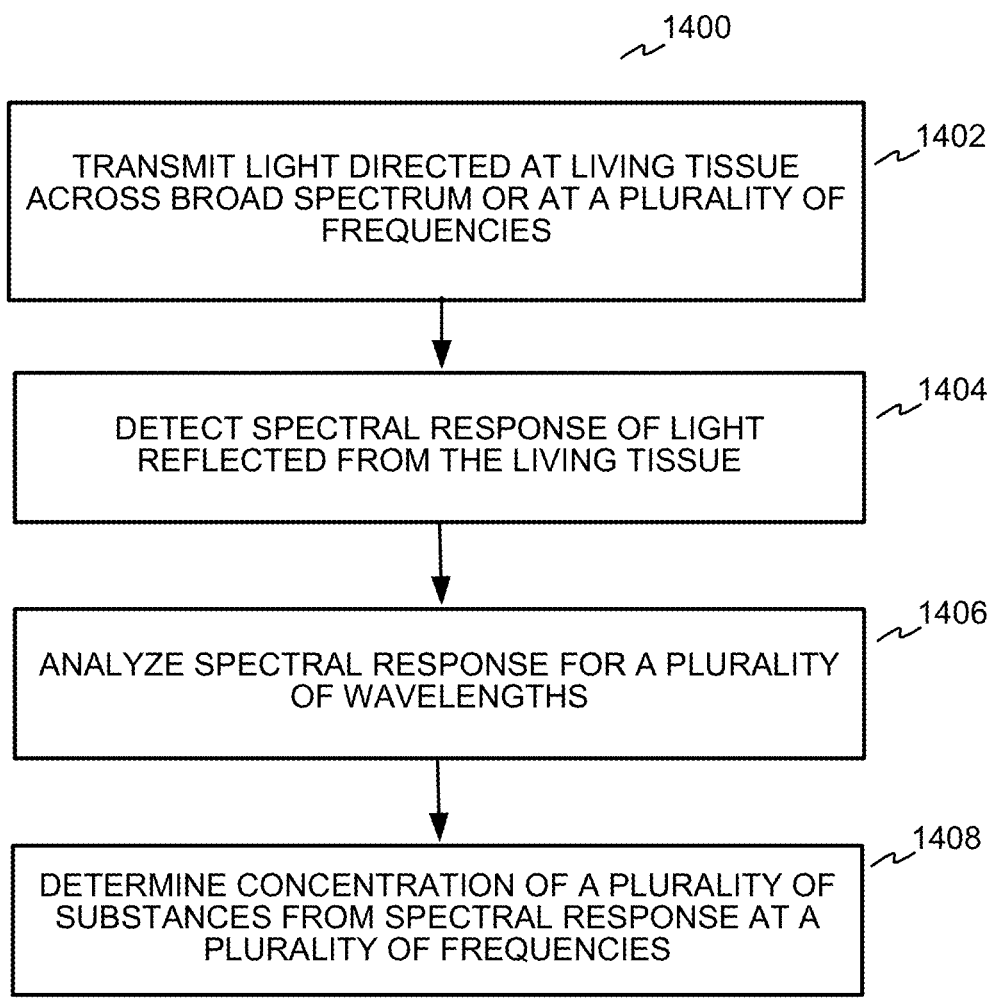
FIG. 14 illustrates a flow diagram of an embodiment of a method for determining biosensor data.

FIG. 14 illustrates a flow diagram of an embodiment of a method 1400 for determining biosensor 500 data. As shown in FIG. 14, one or more of the embodiments of the biosensor 500 described herein is configured to transmit light across a broad spectrum or at a plurality of frequencies at 1402. The biosensor 500 detects the spectral response of the reflected light at 1404 and analyzes the spectral response to determine absorption levels at the plurality of wavelengths or at incremental wavelengths across a broad spectrum at 1406. The absorption levels are measured over one or more cardiac cycles. The systolic and diastolic points of the one or more cardiac cycles are determined with respect to the absorption levels during a cardiac cycle. For example, the absorption levels are aligned in time with the systolic and diastolic points of an arterial pulse waveform during the one or more cardiac cycles. The biosensor 500 is then configured to determine concentration levels of one or more substances in the arterial blood flow at 1408 as described in more detail herein.

For example, the spectral response of arterial blood flow at a first and second wavelength is determined over one or more cardiac cycles. The systolic and diastolic points over the one or more cardiac cycles of the spectral response at the first and second wavelength are determined and aligned with systolic and diastolic points of the arterial blood flow or cardiac cycle. The $L_\lambda$ values are then calculated over a predetermined time period for the first and second wavelength, wherein the $L_\lambda$ values for a wavelength equals:

$$L_\lambda = \log 10(I_{AC+DC}/I_{DC})$$

wherein $I_{AC+DC}$ is the intensity at the wavelength including AC and DC components and $I_{DC}$ is the intensity at the wavelength with the AC filtered by a low pass filter (e.g. 5 Hz low pass filter). The $L_\lambda$ values are calculated using a logarithmic function of the ratio. For example, Beer Lambert L Values $$L^\lambda = \log_{10}(I_{AC+DC}/I_{DC})$$

$\lambda_{IR}$=940 nm (Non-absorbing)
$\lambda_{RED}$=660 nm (Non-absorbing)
$\lambda_{UV-NO}$=390 nm
$\lambda_{UV-NICOTINE}$=260 nm
$\lambda_{YELLOW}$=592 nm
$\lambda_{BLUE}$=468 nm Though log 10 is shown here, the L value may be based on the natural log or other logarithmic function.

Based on the $L_\lambda$ values at two different wavelengths, a ratio R of the $L_\lambda$ values at the two wavelengths may be determined. Depending on the wavelengths, the ratio R may indicate a concentration level or biosensor marker for a substance in arterial blood flow. For example:

Arterial Response R(Ratio) Values $$R(\text{Ratio}) = L^{\lambda_1}/L^{\lambda_2}$$

R value (260 nm/940 nm)~Nicotine Marker
R value (390 nm/940 nm)~Nitric Oxide Marker
R value(468 nm/940 nm)~Liver Enzyme Marker
R value(592 nm/940 nm)~Digestion Marker
R value(660 nm/940 nm)~SpO$_2$ Marker For example, based on unexpected results from clinical trials, it was determined that an R value for at least $L_{390\ nm}/L_{940\ nm}$ may be used as a predictor of high diabetic risk. For example, after 1-2 minutes of PPG data collection at 390 nm and 940 nm, an R value was determined. A Nitric Oxide (NO) R value that is excessively low, taken after a period of fasting of at least four hours of no calorie intake, can indicate a person is at high risk for diabetics due to very low levels of Nitric Oxide in their blood stream. Nitric Oxide (NO) is a naturally occurring vascular dilator and within certain ranges is indicative for normally healthy patients. However very low levels of NO in a blood stream indicates a diabetic pre-cursor and very high NO levels indicate other possible conditions such as blood infections such as sepsis. An NO R value less than 1 or approximately 0.5 was a good indicator that a person has diabetes or early onset of diabetes. An NO R value of 2 or above was a good indicator that a person had a lower risk of diabetes diagnosis. An NO R value in the 5-6 range showed an extremely healthy person with no sign of diabetes. An NO R value in the range 20-200 can show very high risk of cardiovascular event and emergency treatment must be implemented. Thus, a non-invasive, quick 1-2 minute test produced a good indication of cardiovascular risk.

Likewise it is possible to also monitor an individual's Nicotine level within their blood stream and surrounding skin tissue using similar methods by measuring 1-2 minutes of PPG data collection at 260 nm and 940 nm, to determine their Nicotine R value. It is not necessary for Nicotine measurement to be done after period fasting. It can be taken anytime. The Nicotine R(260 nm/940 nm) value is proportional to the level of Nicotine present in their arterial blood and surrounding tissue. This Nicotine R value can be also used to regulate amount of Nicotine into the blood by providing feedback to an Inhalation treatment device. This can be very valuable tool to assist a person of interest in their treatment program to quit smoking by being able to provide measureable results to a care provider. Since the Nicotine is delivered in most cases via smoke inhalation the nicotine is distributed into lungs first, then bloodstream second, and lastly into upper epidermal cells in the skin in this order. Nicotine can be also delivered via nasal spray or gum form. A treatment plan can be likewise constructed to assist users to adjust their dosage until dependency is no longer needed thru the use of a PPG monitor constructed to monitor the key Nicotine Markers. While the Nicotine Ratio (260 nm/940 nm) is mainly focused on the arterial blood concentration, it is also possible to use the individual L value for Nicotine at 260 nm to measure the relative skin absorption level of Nicotine present in the outer skin layers. Additionally, one can monitor the $I_{DC}$ and $I_{AC}$ levels previously described in this embodiment to determine the absorption rates from arterial blood path back into outer layers of epidermal skin. By monitoring the $I_{DC}$ and $I_{AC}$ levels it is possible to see the direct coloration of the nicotine transfer & absorption rates between the arterial blood vessels and the outer skin layers. By comparing the $L_{Nicotene}$ values and the corresponding $I_{DC}$ & $I_{AC}$ values, one can monitor the relative nicotine transfer between the arterial blood and the outer epidermal skin layers and likewise the Nicotine R (260 nm/940 nm) ratio can be used to only focus on the arterial blood flow measurements.

In another embodiment, an R value for at least $L_{468\ nm}/L_{940\ nm}$ may be used as a liver enzyme marker, e.g. P450 enzyme indicator. In another embodiment, an R value for at least $L_{592\ nm}/L_{940\ nm}$ may be used as a digestive indicator.

In one or more aspects, the R value may then be used by a doctor, e.g. during an examination, to determine whether further testing, e.g. for diabetes, needs to be performed. For example, upon detection of a low R value, a doctor may then determine to perform further testing and monitoring with glucose ingestion over a longer period of time using the biosensor 500 or other testing.

In particular, in unexpected results, it is believed that nitric oxide NO levels in the arterial blood flow is being measured at least in part at $L_{390\,nm}$. Since NO is a gas, the NO levels of in vitro blood samples, e.g. from a finger prick, are not detected as the gas dissipates. The NO levels are an indication of insulin concentration in the blood as well as compounds like nicotine in higher concentrations.

Thus, the $L_{390\,nm}$ values are the first time NO levels in vivo, e.g., in arterial blood flow, have been measured directly and correlated with insulin levels, and cardiovascular and diabetic risk. These unexpected results have advantages in early detection of diabetic risk and early detection of cardiac issues related to increased nitrates in the blood stream due to heavy smoking or specific medicines causing high NO levels in the blood stream.

Though $L_{940\,nm}$ values are used at 940 nm, any non-absorbing wavelength may be used for the target substance, such as L values at 660 nm.

The biosensor 500 may also be used to determine alcohol levels in the blood using wavelengths at 390 and/or 468 nm. It is also foreseen that other proteins or compounds, such as those present or with higher concentrations in the blood with persons having cancer, may be detected using similar absorption spectrometry at one or more other wavelengths. Cancer risk may then be determined in a 1-2 minute non-invasive testing using the biosensor 500. Since the biosensor 500 may operate in multiple frequencies, various health monitoring tests may be performed concurrently.

In an embodiment, when a broad spectrum light source is implemented, such as a white light to infrared (IR) or near IR light source, is implemented, the spectral response of the reflected light is then measured across the wavelengths in the broad spectrum, e.g. from 350 nm to 2500 nm, concurrently. In one aspect, the L values are calculated at incremental wavelengths, such as at 1 nm or 1.5 nm or 2 nm incremental wavelengths. In another embodiment, the L values are calculated for a set of predetermined wavelengths. Using the absorption coefficients for substances at the set of predetermined wavelengths, the concentrations of the substances may then be determined.

The intensity of light at a plurality of wavelengths may be due to absorption by a single substance in the arterial blood flow. For example, a single substance may absorb or reflect a plurality of different wavelengths of light. In this example then, $$LN(I_{1-n}) = \mu_1 * C + \mu_2 * C + \mu_3 * C \ldots + \mu_n * C$$

wherein, $I_{1-n}$=intensity of light at wavelengths $\lambda_{1-n}$ $\mu_n$=absorption coefficient of a substance at wavelengths $\lambda_{1-n}$ C=Concentration level of a substance When the absorption coefficients $\mu_{1-n}$ of the single substance are known at the wavelengths $\lambda_{1-n}$, then the concentration level C of the substance may be determined from the spectral response for each of the wavelengths (and in one aspect including a range of 1 nm to 50 nm around each of the wavelengths). Using the spectral response at multiple frequencies provides a more robust determination of the concentration level of the substance.

Figure 15:
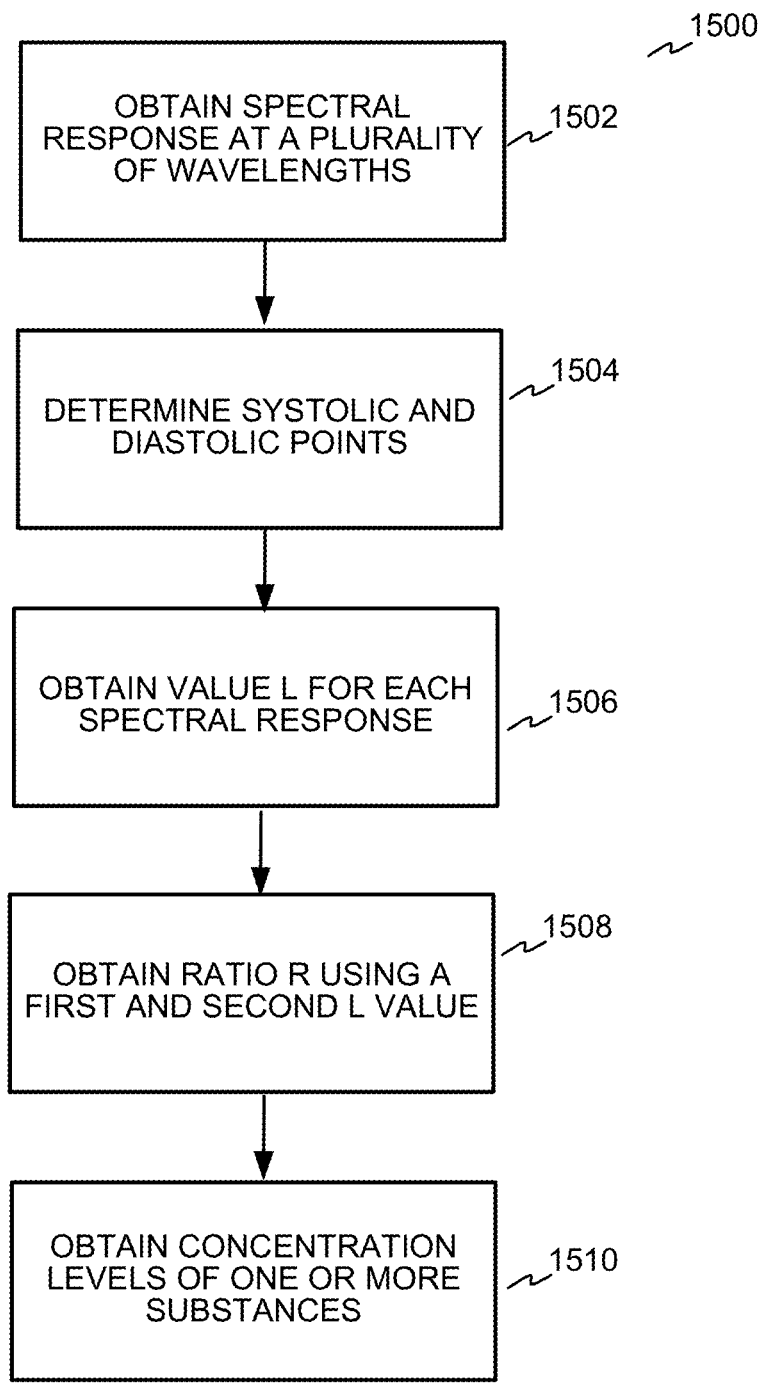
FIG. 15 illustrates a logical flow diagram of an exemplary method to determine blood concentration levels of a plurality of substances using the spectral response for a plurality of wavelength.

FIG. 15 illustrates a logical flow diagram of an exemplary method 1500 to determine blood concentration levels of a plurality of substances using the spectral response for a plurality of wavelengths. The biosensor 500 transmits light directed at living tissue. The light may be across a broad spectrum or at a plurality of discrete frequencies or at a single frequency. For example, the light may be emitted using a broad spectrum light source or multiple LEDs transmitting at discrete wavelengths or a tunable laser transmitting at one or more frequencies. The spectral response of light (e.g. either transmitted through the living tissue or reflected by the living tissue) is obtained at a plurality of wavelengths at 1502. The spectral response is analyzed at the plurality of wavelengths (and ranges of +/−20 to 50 nm around these wavelengths). In one aspect, the systolic and diastolic points are determined at the plurality of wavelengths, e.g. using a peak detection function or other methods at 1504. The L value for each of the plurality of wavelengths is calculated at 1506. In one aspect, the L values are determined at incremental wavelengths, such as at 1 nm or 1.5 nm or 2 nm incremental wavelengths. In another aspect, the L values are calculated for a set of predetermined wavelengths. A ratio R value may also be determined using L values derived from a first spectral response obtained for a first wavelength (and in one aspect including a range of +/−20 to 50 nm) and a spectral response obtained for a second wavelength (and in one aspect including a ranges of +/−20 to 50 nm) at 1508. Based on the R value, a concentration level of one or more substances may be determined at 1510.

Figure 16:
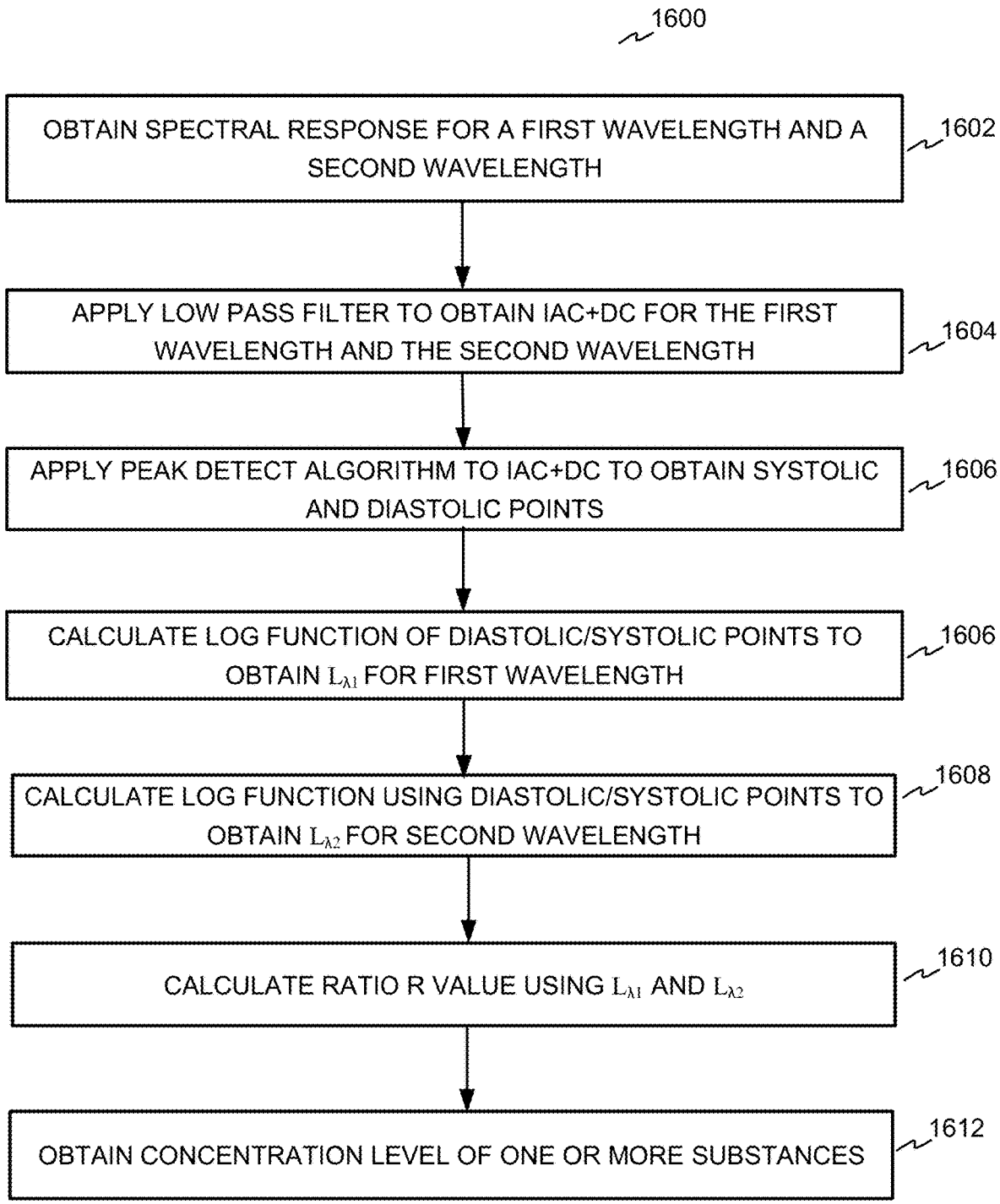
FIG. 16 illustrates a schematic block diagram of an embodiment of a method for determining concentration levels or indicators of substances in pulsating blood flow in more detail.

FIG. 16 illustrates a schematic block diagram of an embodiment of a method for determining concentration levels or indicators of substances in pulsating blood flow in more detail. The biosensor 500 obtains a spectral response signal at a first wavelength and at a second wavelength at 1602. The spectral response signal includes AC and DC components $I_{AC+DC}$. A low pass filter is applied to the spectral response signals $I_{AC+DC}$ to isolate the DC component of the spectral response signals at each wavelength at 1604. The AC fluctuation is due to the pulsatile expansion of the arteriolar bed when the volume of arterial blood increases. In order to measure the AC fluctuation, measurements are taken at different times and a peak detection algorithm or other means is used to determine the diastolic point and the systolic point of the spectral responses at 1606. The systolic and diastolic measurements are compared in order to compute the L values using Beer-Lambert equations. For example, a logarithmic function may be applied to the ratio of $I_{AC+DC}$ and $I_{DC}$ to obtain an L value for the first wavelength $L\lambda 1$ at 1606 and for the second wavelength $L\lambda 2$ at 1608. The ratio R of the first wavelength $L\lambda 1$ and for the second wavelength $L\lambda 2$ may then be calculated at 1610.

Various unexpected results were determined from clinical trials using the biosensor 500. In one aspect, based on the clinical trials, an R value obtained from the ratio $L\lambda 1=390$ nm and $L\lambda 2=940$ was found to be a predictor or indicator of diabetic risk or diabetes as described in more detail herein. In another aspect, based on the clinical trials, the R value obtained from the ratio of L468 nm/L940 nm was identified as an indicator of the liver enzyme marker P450. In another aspect, based on the clinical trials, the R value obtained from the ratio of L592 nm/L940 nm was identified as an indicator of digestion phases, such as phase 1 and phase 2, in the arterial blood flow. In another aspect, the R value from the ratio of L660 nm/L940 nm was found to be an indicator of oxygen saturation levels SpO2 in the arterial blood flow. In another aspect, it was determined that the biosensor 500 may determine alcohol levels in the blood using spectral responses for wavelengths at 390 and/or 468 nm. In general, the second wavelength of 940 nm is selected because it has a low absorption coefficient for the targeted substances described herein. Thus, another wavelength other than 940 nm with a low absorption coefficient for the targeted substances (e.g. at least less than 25% of the absorption coefficient of the targeted substance for the first wavelength) may be used instead. For example, the second wavelength of 940 nm may be replaced with 860 nm that has a low absorption coefficient for the targeted substances. In another aspect, the second wavelength of 940 nm may be replaced with other wavelengths, e.g. in the IR range, that have a low absorption coefficient for the targeted substances. In general, it is desired that the spectral response for the first predetermined wavelength have a higher intensity level than the spectral response for the second predetermined wavelength.

In another aspect, it was determined that other proteins or compounds, such as those present or with higher concentrations in the blood with persons having cancer, may be detected using similar PPG techniques described herein with biosensor 500 at one or more other wavelengths. Cancer risk may then be determined using non-invasive testing over a short measurement period of 1-10 minutes. Since the biosensor 500 may operate in multiple frequencies, various health monitoring tests may be performed concurrently. For example, the biosensor 500 may measure for diabetic risk, liver enzymes, alcohol levels, cancer risk or presence of other analytes within a same measurement period using PPG techniques.

Figure 17:
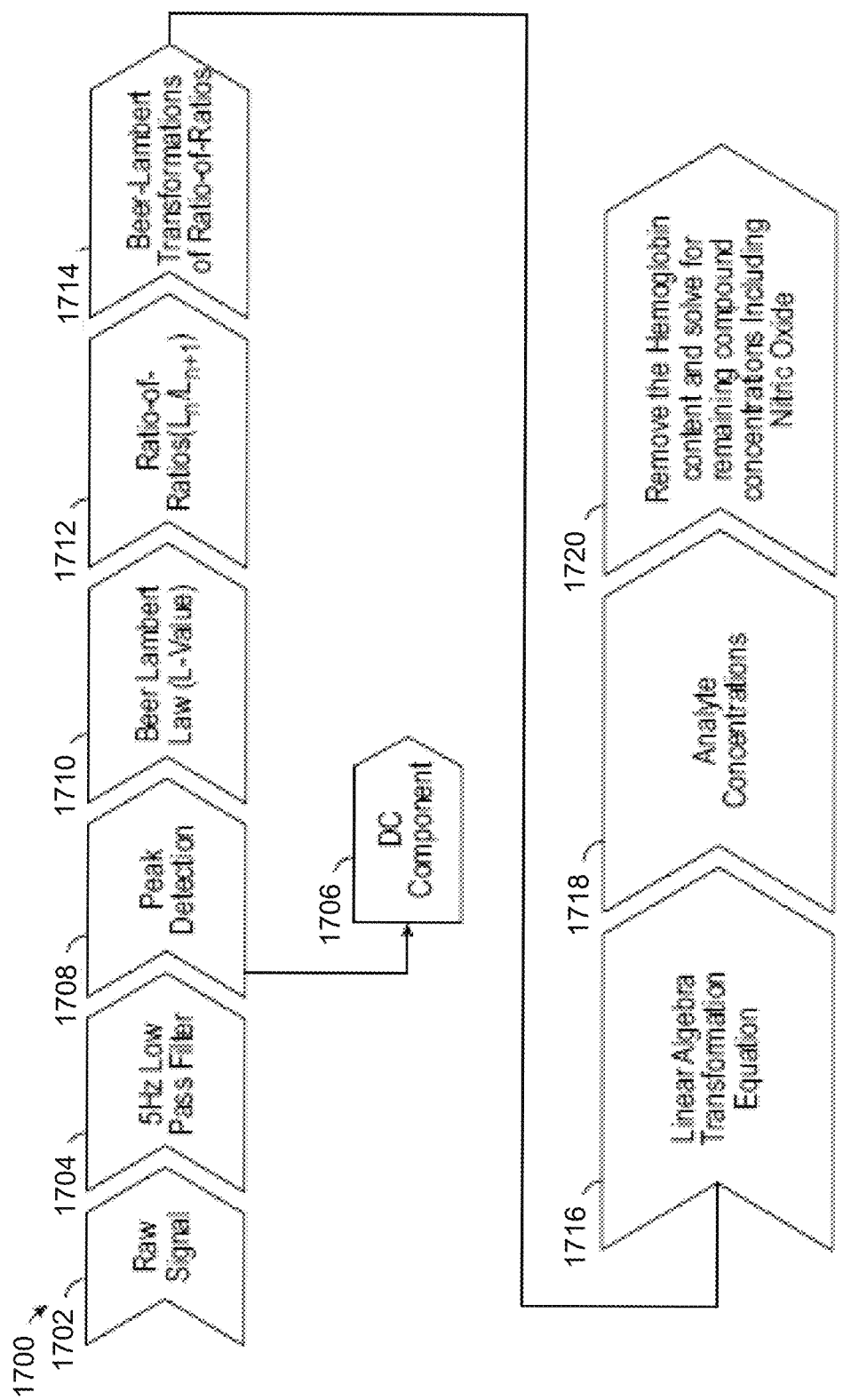
FIG. 17 illustrates a schematic block diagram of an embodiment of a method for determining concentration levels or indicators of substances in pulsating blood flow in more detail.

FIG. 17 illustrates a schematic block diagram of an embodiment of a method 1700 for determining concentration levels or indicators of substances in pulsating blood flow in more detail. The biosensor 500 obtains raw signal including a spectral response signal at a first wavelength and at a second wavelength at 1702. The spectral response signal includes AC and DC components IAC+DC. A low pass filter, such as a 5 Hz low pass filter, is applied to the spectral response signal IAC+DC to isolate the DC component 1706 of the spectral response signal at each wavelength at 1704. The AC fluctuation is due to the pulsatile expansion of the arteriolar bed due to the volume increase in arterial blood. In order to measure the AC fluctuation, measurements are taken at different times and a peak detection algorithm or other means is used to determine the diastolic point and the systolic point of the spectral response at 1708. The systolic and diastolic measurements are compared in order to compute the L values using Beer-Lambert equations at 1710. For example, a logarithmic function may be applied to the ratio of $I_{AC+DC}$ and $I_{DC}$ to obtain an L value for the first wavelength $L_{\lambda,1}$ and for the second wavelength $L_{\lambda,2}$. The ratio R of the first wavelength $L_{\lambda,1}$ and for the second wavelength $L_{\lambda,2}$ may then be calculated at 1712. The ratio R may be transformed using Beer Lambert transformations in 2414 to calibrate for tissue properties. When multiple frequencies are used to determine a concentration level of one or more substances, linear functions are applied at 1716, and the one or more concentration levels of the substances or analytes are determined at 1718.

In an embodiment, a substances or analyte may be attached in the blood stream to one or more hemoglobin compounds. The concentration level of the hemoglobin compounds may then need to be subtracted from the concentration level of the substance determined at 1718 to isolate the concentration level of the substance at 1720 from the hemoglobin compounds. For example, nitric oxide (NO) is found in the blood stream in a gaseous form and also attached to hemoglobin compounds. Thus, the measurements at $L_{390\ nm}$ to detect nitric oxide may include a concentration level of the hemoglobin compounds as well as nitric oxide. The hemoglobin compound concentration levels may then be determined and subtracted to isolate the nitric oxide concentration levels. The hemoglobin compounds include, e.g., Oxyhemoglobin [HbO2] 3202, Carboxyhemoglobin [HbCO] 3204, Methemoglobin [HbMet], and reduced hemoglobin fractions [RHb]. The biosensor 500 may control the PPG circuit 1020 to detect the total concentration of the hemoglobin compounds using a center frequency of 660 nm and a range of 1 nm to 50 nm. A method for determining the relative concentration or composition of different kinds of hemoglobin contained in blood is described in more detail in U.S. Pat. No. 6,104,938 issued on Aug. 15, 2000, which is hereby incorporated by reference herein.

Though the above description includes details with respect to pulsating arterial blood flow, the biosensor 500 may use similar techniques described herein for pulsating venous blood flow. The biosensor 500 is positioned on skin tissue over veins, such as on the wrist, and spectral responses obtained from light reflected by or transmitted through the pulsating venous blood flow. In addition, the biosensor 500 may use similar techniques described herein for surrounding tissue.

Figure 18:
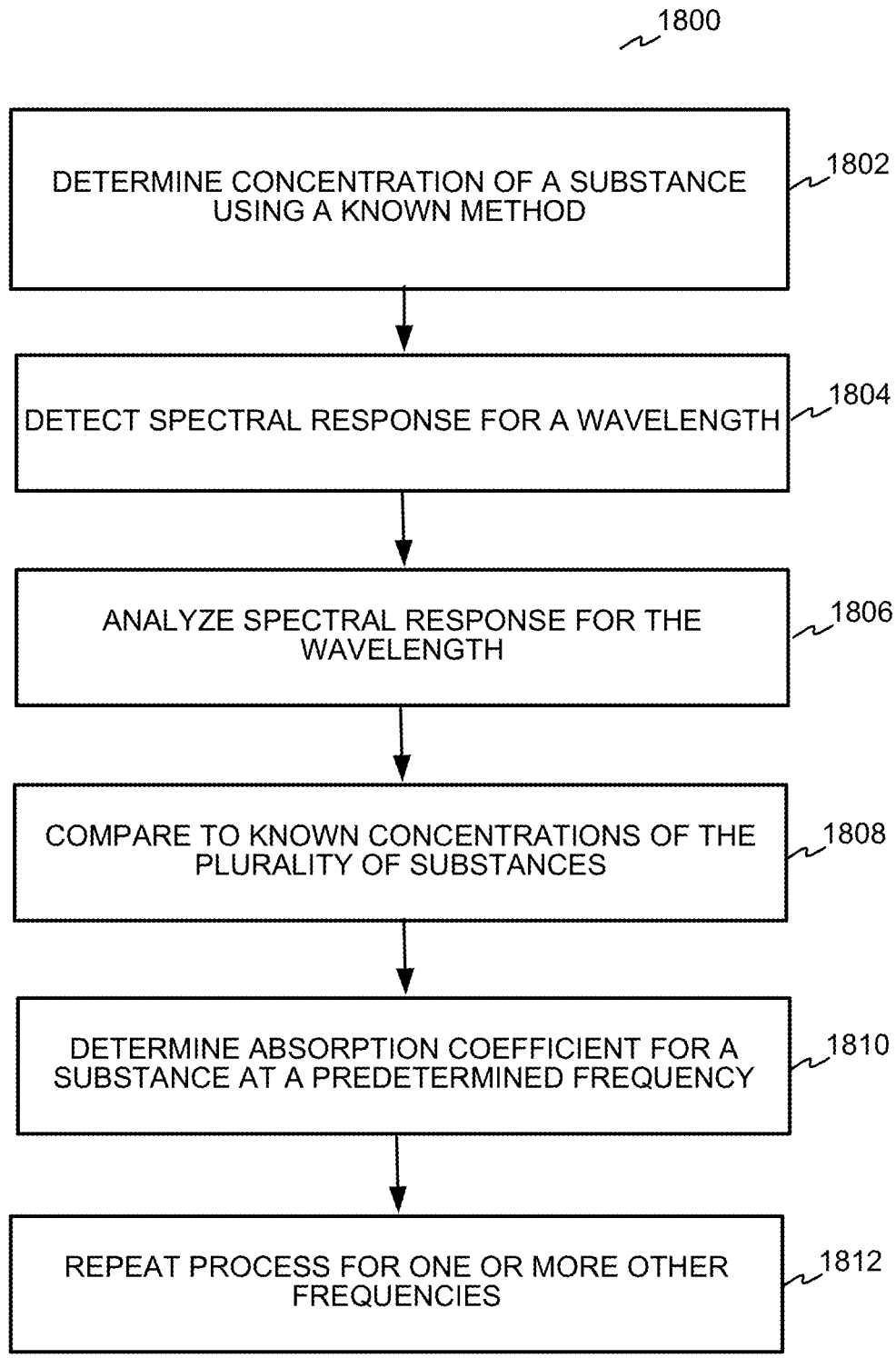
FIG. 18 illustrates a logical flow diagram of an exemplary method to determine an absorption coefficients $\mu$ of a substance at a wavelength $\lambda$.

FIG. 18 illustrates a logical flow diagram of an exemplary method 1800 to determine an absorption coefficients μ of a substance at a wavelength λ. The concentration level of a substance in arterial blood is obtained using a known method at 1802. For example, blood may be extracted at predetermined intervals during a time period and a blood gas analyzer may be used to measure a concentration level of a substance. The biosensor 500 emits light at a wavelength (and in one aspect for a range of 1 nm-50 nm around the wavelength) and detects a spectral response for the wavelength (and in one aspect for a range of 1 nm-50 nm around the wavelength) at 1804. The spectral response for the predetermined wavelength is analyzed at 1806. The intensity of the detected light is determined. The intensity of the detected light is compared to the known concentration level of the substance at 1808. The absorption coefficient for the substance may then be determined using the Beer-Lambert equations described herein at 1810.

The above process may be repeated at one or more other frequencies at 1812. For example, as described herein, the spectral analysis over a range or at multiple frequencies may be analyzed to determine one or more frequencies with a higher intensity or power level in response to a concentration level or presence of the substance. Thus, one or more frequencies may be analyzed and identified for detection of the substance, and the absorption coefficient for the substance determined at the one or more frequencies.

In another embodiment, the concentration level of a substance may be obtained from predetermined values obtained through experimentation. For example, in a calibration phase, a correlation table may be compiled through experimentation that includes light intensity values I1-$n$ at one or more wavelengths λ1-$n$ and a corresponding known concentration level for the substance for the light intensity values. In use, the biosensor 500 detects a spectral response and determines the light intensity values I1-$n$ at one or more wavelengths λ1-$n$. The biosensor 500 then looks up the detected light intensity values I1-$n$ in the correlation table to determine the concentration level of the substance.

Figure 19:
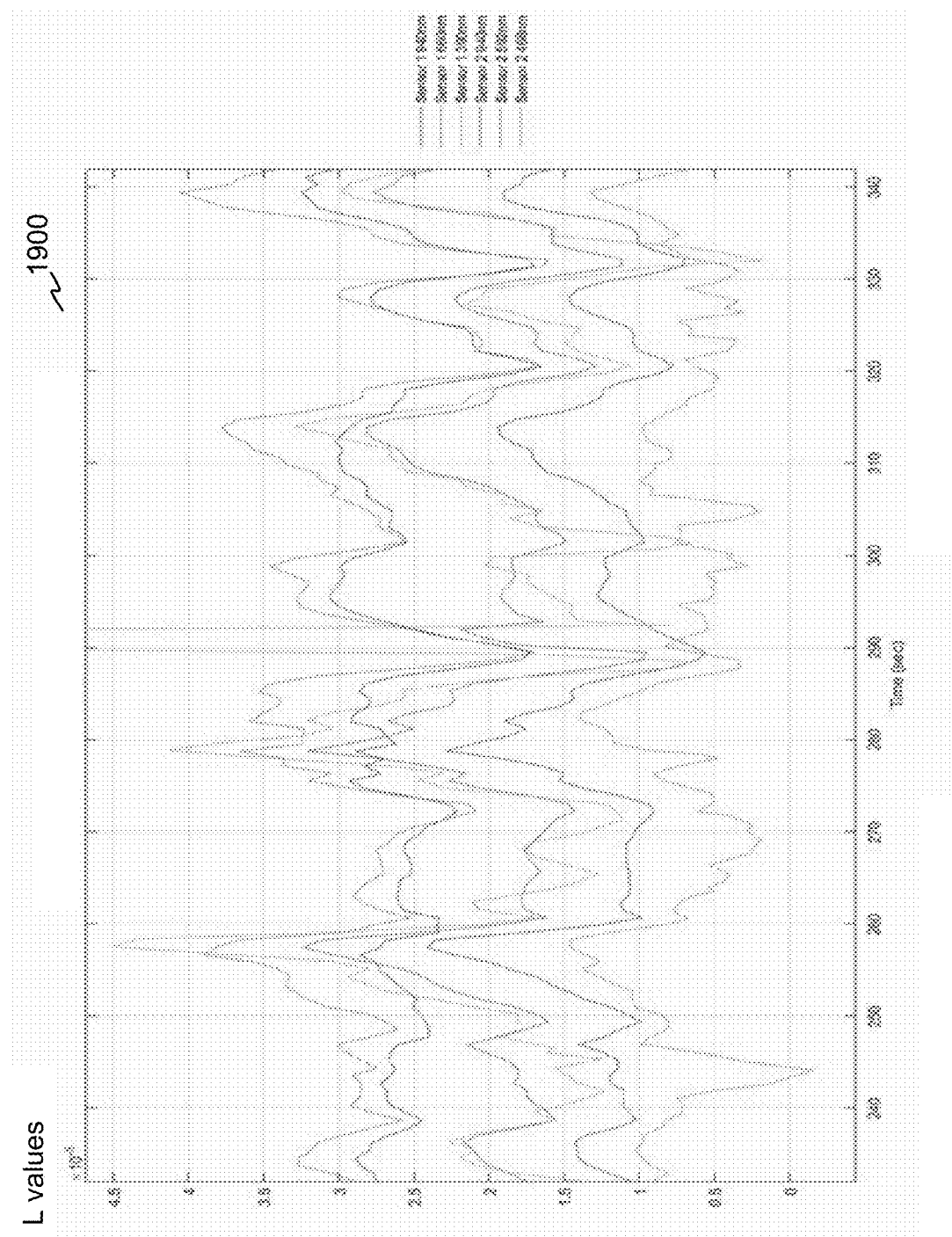
FIG. 19 illustrates an exemplary graph of spectral responses of a plurality of wavelengths from clinical data using the biosensor.

FIG. 19 illustrates an exemplary graph 1900 of spectral responses of a plurality of wavelengths from clinical data using the biosensor 500. In this embodiment, the spectral response of a plurality of wavelengths was measured using the biosensor 500 over a measurement period of almost 600 seconds or approximately 10 minutes. The graph 1900 illustrates the L values calculated from the spectral response for a first wavelength of approximately 940 nm, the spectral response for a second wavelength of approximately 660 nm and the spectral response for a third wavelength of approximately 390 nm obtained from a first biosensor 500 measuring reflected light from a first fingertip of a patient. The graph further illustrates the spectral response for a fourth wavelength of approximately 592 nm and a fifth wavelength of approximately 468 nm and the spectral response 1408 again at 940 nm obtained from a second biosensor 500 measuring reflected light from a second fingertip of a patient. The spectral responses are temporally aligned using the systolic and diastolic points. Though two biosensor 500s were used to obtain the spectral responses in this clinical trial, a single biosensor 500 may also be configured to obtain the spectral responses of the plurality of wavelengths.

Figure 20:
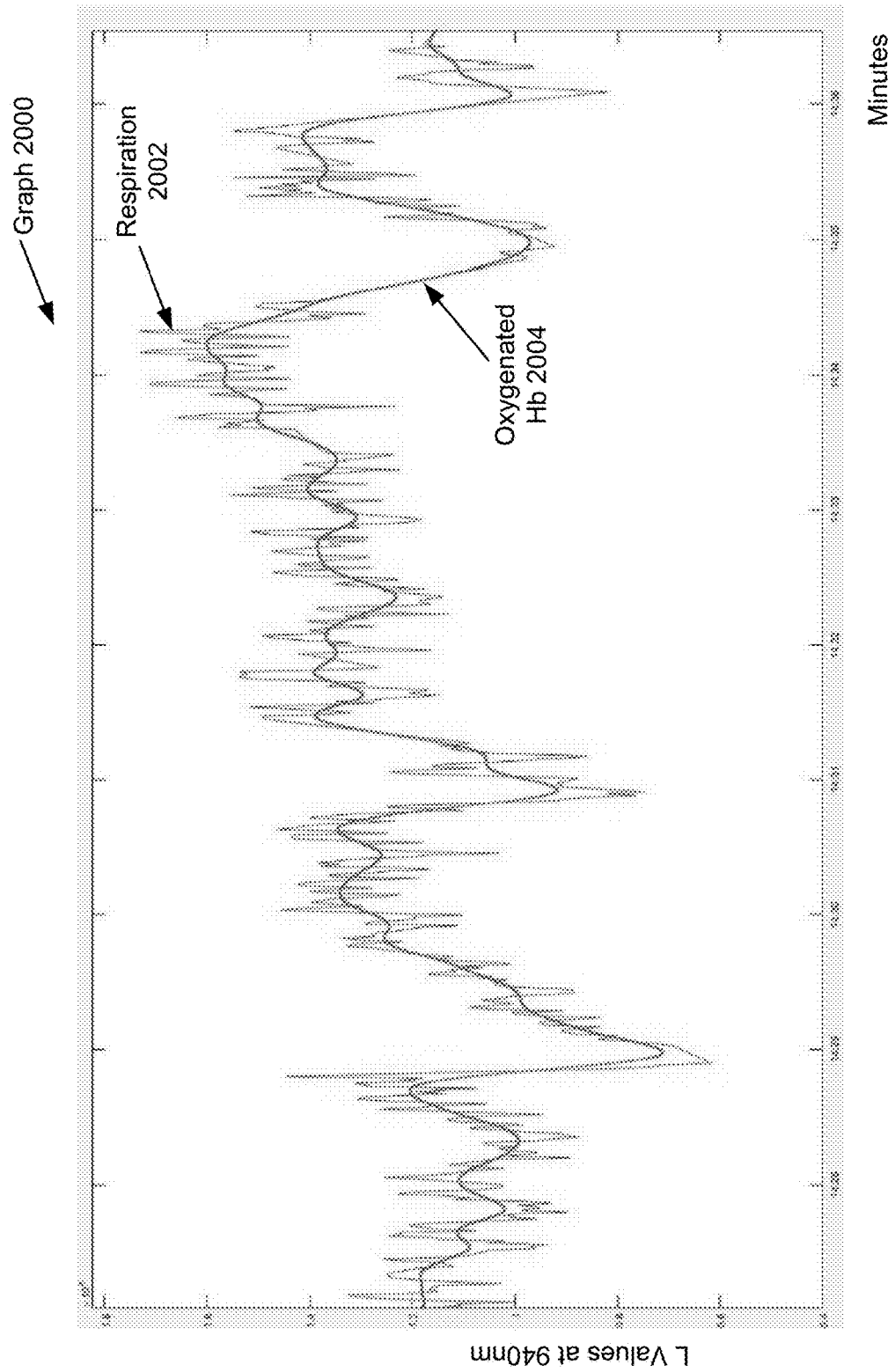
FIG. 20 illustrates an exemplary graph of L values determined from spectral responses detected around a predetermined wavelength from clinical data using an example biosensor.

FIG. 20 illustrates an exemplary graph of L values determined from spectral responses detected around a predetermined wavelength from clinical data using an example biosensor 500. In this example, the predetermined wavelength is approximately 940 nm but other wavelengths may also be used. The first line graph 2002 indicates the L values of the spectral responses over a period of approximately 10 minutes. The L values may be used to indicate respiration or breathing cycles. For example, inhalation periods are shown in the line graph 2002 as it moves from a low point to a high point. The exhalation periods are shown in the line graph 2004 as it moves from a high point to a low point. The difference between the low points and high points indicates a length or depth of the inhalation or exhalation. For example, at approximately 14.29 minutes, the L value drops significantly over several seconds. This drop indicates a long period without an inhalation, such as holding a breath. An average or mean of inhalation periods over a time period may be used to determine a respiration rate. The second line graph 2004 indicates the oxygenated hemoglobin determined from the L values. The PPG circuit 1020 may thus be used to determine an inhalation period, an exhalation period and a respiration rate.

Figure 21:
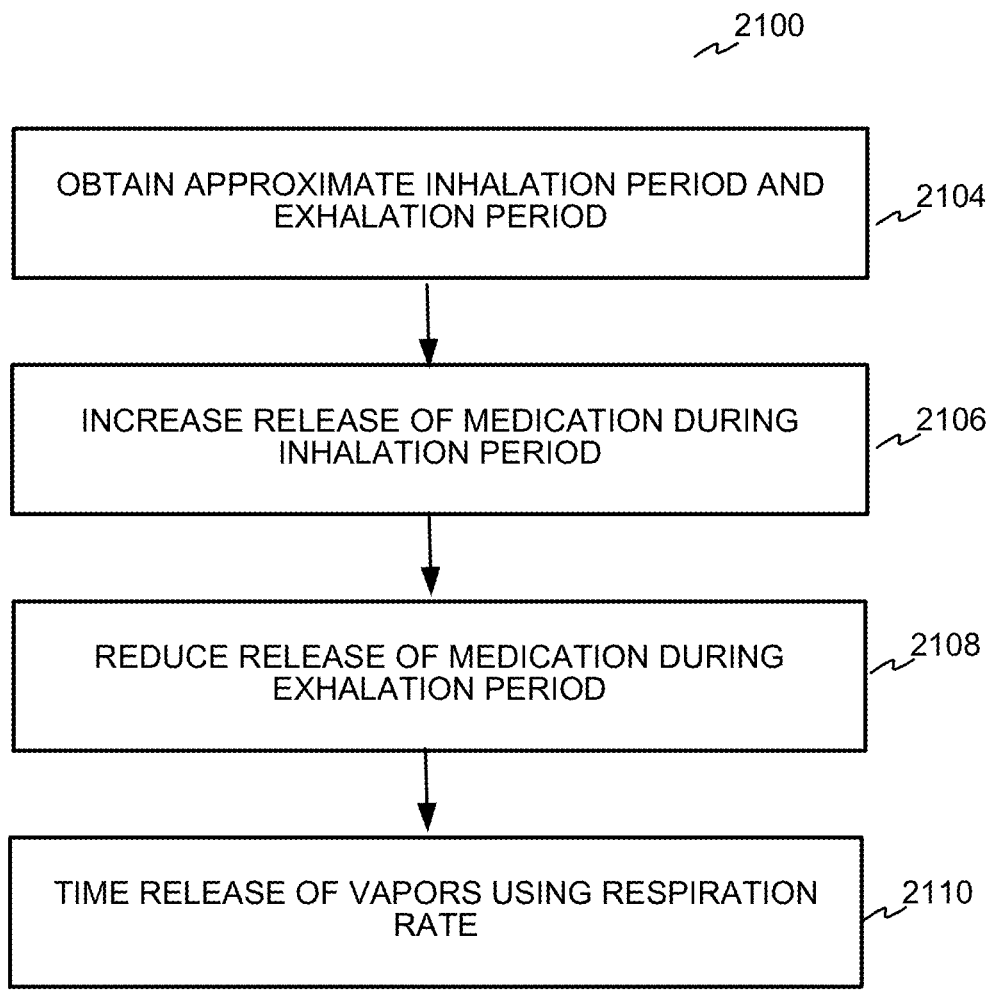
FIG. 21 illustrates a logical flow diagram of an exemplary method of operation of the atomizer.

FIG. 21 illustrates a logical flow diagram of an exemplary method 2100 of operation of the atomizer 150. An approximate inhalation period and/or exhalation period is obtained at 2104, e.g. using the biosensor 500 or pressure sensor 148. The atomizer 150 increases release or production of the vapor during an inhalation period at 2106. For example, the atomizer 150 increases heat of the heating element 214 to increase atomization of the fluid into vapor. The production of the vapor increases such that an amount of the vapor at the mouthpiece is increased during an inhalation period at 2106.

In another example, the atomizer 150 controls a production of vapor to decrease an amount of the vapor during an exhalation period at 2108. For example, the atomizer 150 decreases heat of the heating element 214 to decrease or halt atomization of the fluid into vapor during exhalation.

The atomizer 150 may additionally or alternatively control production of vapor in response to a respiration rate at 2110. For example, the atomizer 150 increases and decreases heat of the heating element at the approximate respiration rate.

FIG. 22 illustrates a logical flow diagram of an exemplary method 2200 of operation of the atomizer 150 using the biosensor 500. In an embodiment, the biosensor 500 monitors concentration of relevant substances in arterial blood flow at 2202 as described herein. For example, when the vapor includes an atomized medication, the biosensor 500 550 may monitor a concentration level of the medication in the blood flow or tissue. As a patient inhales the vapor including the atomized medication over the course of a treatment, the concentration or level of the medication increases in the blood flow. The biosensor 500 150 may monitor the concentration level in the blood flow to determine an efficacy of the medication.

In addition or alternatively, a concentration level of the medication may also be determined in surrounding tissue. If the blood vessels transfer the medication to tissue cells, this concentration of the medication may be detected in the tissue by the biosensor 500 as well. The biosensor 500 determines an L value with a high absorption coefficient value for the medication and an L value with a low absorption coefficient of tissue. The ratio of the L values will provide an indication of the concentration level of the medication in tissue. The concentration level of the medication in the blood vessels may need to be subtracted or otherwise considered in the determination.

The rate of increase of concentration of the medication in the tissue may be determined to generate an absorption rate of the medication. The absorption rate of medication by the tissue may help in determining dosages and treatment lengths.

The biosensor 500 may further monitor patient vitals at 2204. For example, the patient vitals may include temperature, blood pressure, pulse, respiration rate, etc. The biosensor 500 may monitor and determine when one or more predetermined thresholds of the patient vitals or concentration of relevant substances is reached at 2206. For example, the biosensor 500 may detect a high blood pressure or pulse that exceeds a predetermined threshold. The biosensor 500 then deactivates operation of the atomizer 150 at 2208. The biosensor 500 may detect an unsafe level of medication or other substance in the blood flow or surrounding tissue in 2206 and deactivate operation of the atomizer at 2208.

Figure 23:
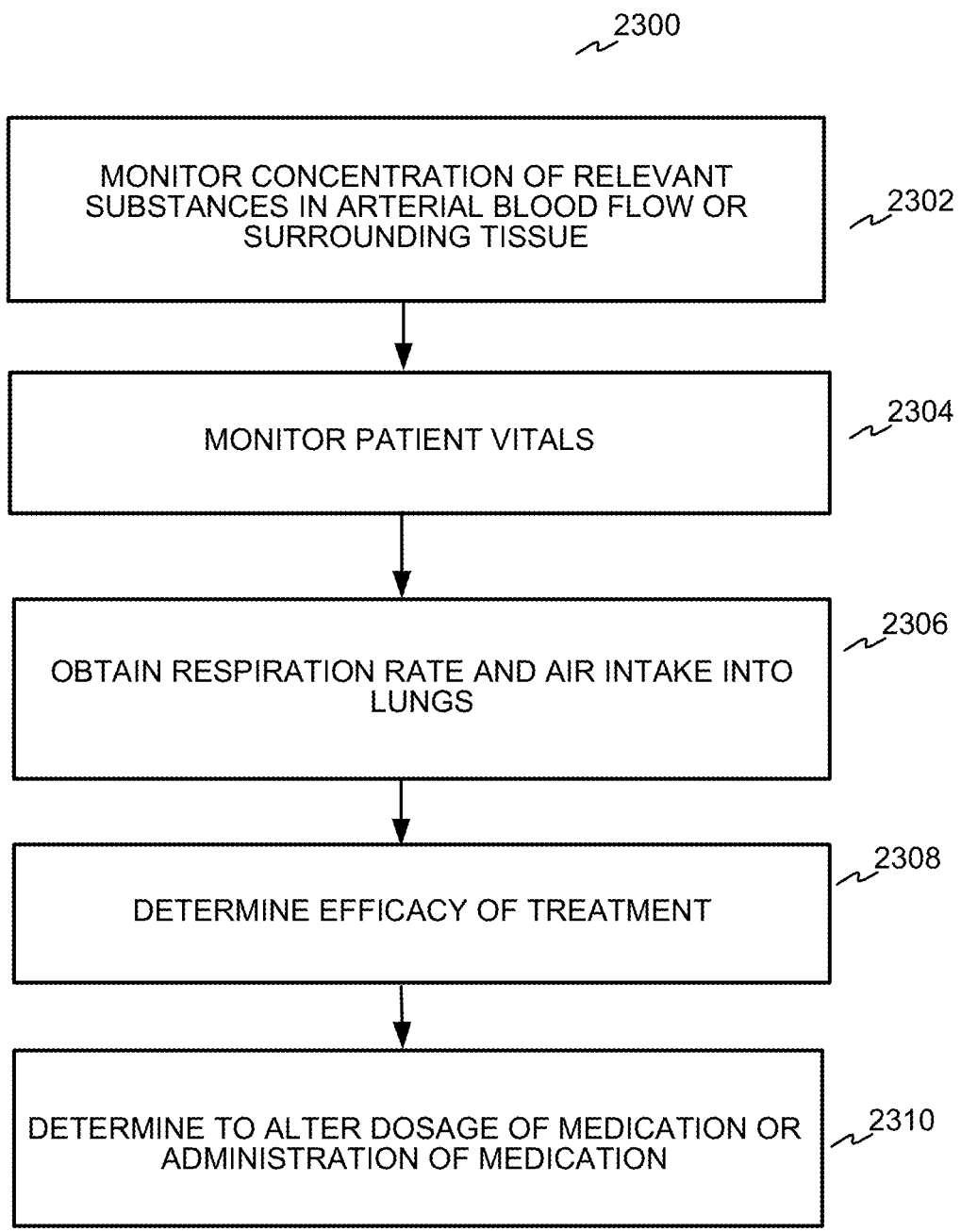
FIG. 23 illustrates a logical flow diagram of an exemplary method of operation of the atomizer using the biosensor.

FIG. 23 illustrates a logical flow diagram of an exemplary method 2300 of operation of the atomizer 150 using the biosensor 500. The biosensor 500 monitors concentration of relevant substances in arterial blood flow and/or surrounding tissue at 2302. For example, when the fluid includes nicotine, nicotine levels in the arterial blood flow and/or surrounding tissue is monitored. In another example, the fluid may include medication to treat asthma, COPD, respiratory infection, allergic reaction, etc. The biosensor 500 may then monitor the concentration of the medication or other relevant substances in arterial blood flow and/or surrounding tissue.

The biosensor 500 may further monitor patient vitals at 2304. The respiration rate may be determined from the pressure sensor or the biosensor 500. In addition, based on biosensor 500 data such as the L values shown in FIG. 20, the air intake into the lungs of the patient may be assessed, such as breathing deeply or shallow breaths. The efficacy of treatment may thus be determined using one or more of the patient vitals, respiration rate, air intake, and concentration of relevant substances in the blood vessels or surrounding tissue. A caregiver may review this data and other symptoms over a period of time. The caregiver may then determine to alter treatment of the patient. For example, a type or a dosage of medication in the cartridge 100 mat be altered or rate of release of medication by the atomizer 150 may be increased or decreased. The caregiver may determine to alter a timing of administration, such as longer periods of treatment or more frequent periods of treatment. The biosensor 500 thus provides biosensor 500 data to assist in determining an efficacy of treatment.

Figure 24:
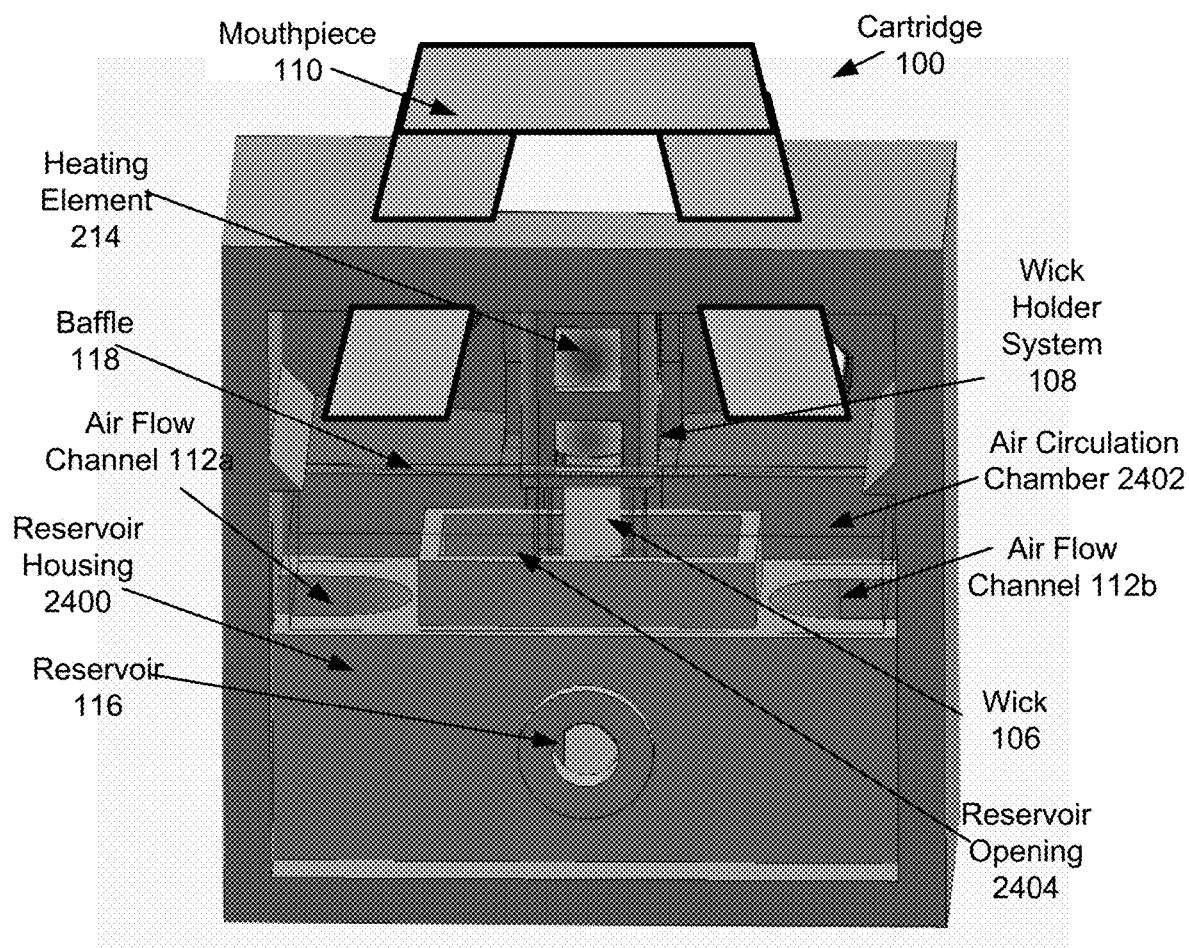
FIG. 24 illustrates an elevational view of an embodiment of a cartridge.

FIG. 24 illustrates a schematic block diagram of another embodiment of a cartridge 100. The cartridge includes a mouthpiece 110, a wick 106 and wick holder system 108. The cartridge includes a baffle 118 that extends across one or more openings of the mouthpiece 110. The baffle 118 is positioned roughly horizontally from one side of the cartridge to another side of the cartridge 100 and forms an opening for the wick 106 to extend from the wick holder system 108 into the reservoir 116.

A reservoir housing 2400 forms one or more air flow channels 112a, 112b and a reservoir opening 2404. The wick 106 extends from the wick holder system 108 at a top portion of the cartridge 100 through the reservoir opening 2404 to the reservoir 116. The reservoir 116 includes fluid for atomization by the heating element 214. An air circulation chamber 2402 is formed between the baffle 118 and reservoir housing 2400. The air circulation chamber 2402 is configured to enhance air recirculation and mixing of hot atomized gases to allow some cooling effect to the turbulent vapors prior to inhalation. The baffle 118 also helps to isolate the fluid from the mouthpiece 110 to help prevent unintended leakage to the user. Any droplets or fluid flowing into the air circulation chamber 2402 or above the baffle 118 is channeled to flow back into the reservoir 116 through the reservoir opening 2402.

Figure 25:
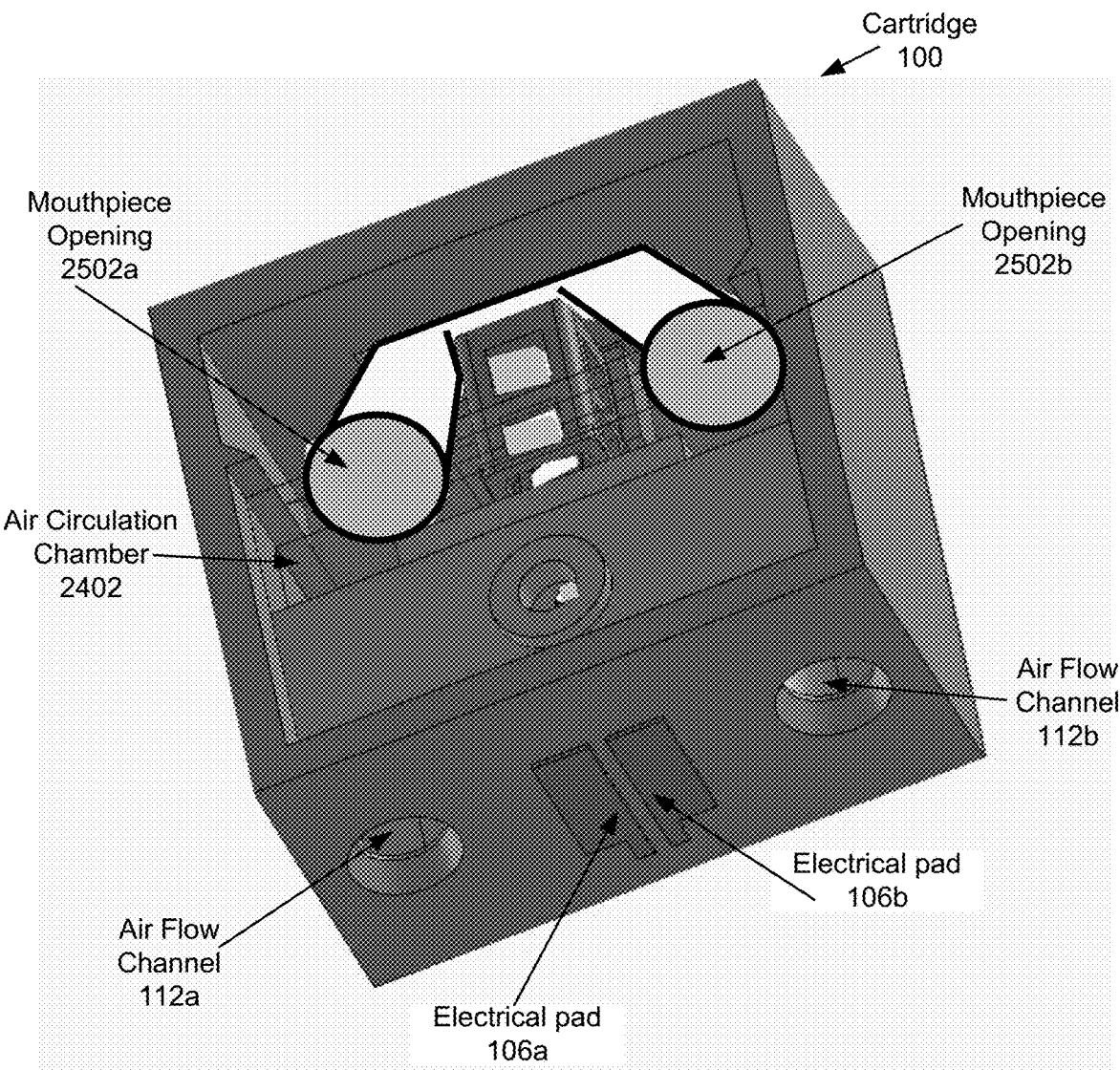
FIG. 25 illustrates another elevational view of an embodiment of a cartridge

FIG. 25 illustrates a schematic block diagram of another embodiment of a cartridge. The mouthpiece 110 includes a first mouthpiece opening 2502a and a second mouthpiece opening 2502b. The first set of baffles 118a, 188b create two air chambers in the cartridge 100, wherein each chamber includes at least one of the mouthpiece openings 2502a, 2502b. The two chambers and mouthpiece openings 2502a, 2502b form a dual channel air flow path for enhanced delivery of the atomized vapors into deep lung areas.

In one or more aspects herein, a processing circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

What is claimed is:

1. An atomizer, comprising:
   a cartridge configured to hold a fluid;
   an atomizer system configured to atomize the fluid in the cartridge into a vapor for inhalation;
   a biosensor including a sensor circuit that emits a first wavelength of light at tissue of a user and generates at least a first spectral response around the first wavelength of light reflected from the tissue of the user; and
   a processing circuit configured to:
      determine a respiration rate of the user using the first spectral response;
      determine an inhalation period and exhalation period from the respiration rate; and
      control the atomizer system to increase atomization of the vapor during the inhalation period and decrease atomization of the vapor during the exhalation period.

2. The atomizer of claim 1, wherein the atomizer further comprises:
   a fluid sensor configured to detect an indicator of an amount of fluid in the cartridge; and
   wherein the processing circuit is further configured to:
      determine the indicator of the amount of fluid in the cartridge reaches a predetermined level; and
      deactivate the atomizer system in response to the indicator of the amount of fluid in the cartridge reaching the predetermined level.

3. The atomizer of claim 2, wherein the atomizer system comprises:
   a wick for absorbing fluid in the cartridge; and
   a heating element in contact with the wick, wherein the heating element increases in heat to atomize the fluid absorbed by the wick.

4. The atomizer of claim 3, wherein the fluid sensor comprises:
   an impedance sensor configured to detect an impedance of the wick using the heating element.

5. The atomizer of claim 4, wherein the processing circuit is further configured to control the atomizer to operate in an atomization mode or a measurement mode by:
   activating the atomization system to operate in the atomization mode to atomize the fluid in the cartridge into a vapor for inhalation using the heating element;
   deactivate the atomization system; and
   activate the impedance sensor to detect an impedance of the wick using the heating element.

6. The atomizer of claim 1, wherein the processing circuit is further configured to:
- determine vitals of the user using at least the first spectral response, wherein the vitals include one or more of: respiratory rate, heart rate or blood pressure;
- determine a concentration of a substance in blood flow of vessels of the patient using at least the first spectral response, wherein the substance increases in concentration in the blood flow of the vessels in response to inhalation of the vapor; and
- control the atomizer system to increase atomization of the vapor or decrease atomization of the vapor in response to the concentration level of the substance in the blood flow.

7. The atomizer of claim 6, wherein the sensor circuit is further configured to:
- generate the first spectral response around the first wavelength of light reflected from the tissue of the user;
- generate at least a second spectral response around a second wavelength of light reflected from the tissue of the user; and
- wherein the processing circuit is further configured to:
- obtain a value $L_{\lambda 1}$ using the first spectral response, wherein the value $L_{\lambda 1}$ isolates the first spectral response due to pulsating blood flow;
- obtain a value $L_{\lambda 2}$ using the second spectral response, wherein the value $L_{\lambda 2}$ isolates the second spectral response due to pulsating blood flow;
- obtain a value $R_{\lambda 1,\lambda 2}$ from a ratio of the value $L_{\lambda 1}$ and the value $L_{\lambda 2}$;
- determine the concentration level of the substance in the blood flow from the value $R_{\lambda 1,\lambda 2}$.

8. The atomizer of claim 7, wherein the concentration level of the substance includes at least one of: a blood nicotine level, a liver enzyme level, or a nitric oxide (NO) indicator level.

9. The atomizer of claim 8, wherein the atomizer is configured to alter a dosage, an administration rate or an administration period of the fluid in response to the concentration level of the substance in the blood flow.

10. The atomizer of claim 1, wherein the cartridge includes:
- a chamber between a wick and a port of the cartridge, wherein the chamber is configured to hold the fluid; and
- a heat soluble seal formed between the chamber and the wick, wherein the heat soluble seal comprises a material configured to dissolve upon heating of the wick.

11. The atomizer of claim 1, wherein the cartridge includes:
- a first set of baffles extending across a mouthpiece;
- a second set of baffles extending across air flow channels, wherein the air flow channels prove air into the cartridge; and
- wherein the first set of baffles and the second set of baffles form an air flow chamber configured to enhance mixing of the vapor and air.

12. An atomizer, comprising:
- a cartridge configured to hold a fluid;
- an atomizer system configured to atomize the fluid in the cartridge into a vapor for inhalation, wherein the atomizer system includes:
  - a wick for absorbing fluid in the cartridge; and
  - a heating element in contact with the wick, wherein the heating element increases in heat to atomize the fluid absorbed by the wick;

an impedance sensor configured to detect an indicator of an amount of fluid in the cartridge, wherein the impedance sensor is configured to detect an impedance of the wick using the heating element; and a processing circuit configured to:
activate the atomization system to operate in the atomization mode to atomize the fluid in the cartridge into a vapor using the heating element;
deactivate the atomization system; and
activate the impedance sensor to detect the impedance of the wick using the heating element.

13. The atomizer of claim 12, wherein the processing circuit is further configured to:
obtain an initial impedance of the wick prior to a first atomization mode;
determine the initial impedance is within a predetermined range of impedance measurements; and
initiate the first atomization mode.

14. The atomizer of claim 12, wherein the processing circuit is further configured to:
obtain an initial impedance of the wick prior to a first atomization mode;
determine the initial impedance is not within a predetermined range of impedance measurements; and
prevent the first atomization mode.

15. An atomizer, comprising:
a cartridge configured to hold a medication in a fluid;
an atomizer system configured to atomize the fluid into a vapor for inhalation by a user;
a biosensor including:
a PPG circuit that emits light at a plurality of wavelengths directed to skin tissue of a user and generates a plurality of spectral responses around the plurality of wavelengths from light reflected from the skin tissue of the user;
a processing circuit configured to:
obtain a concentration level of the medication in blood flow of the user using the plurality of spectral responses; and
control the atomizer system to increase or decrease atomization of the vapor in response to the concentration level of the medication in the blood flow of the user.

16. The atomizer of claim 15, wherein the processing circuit is further configured to:
generate an alert in response to the concentration level of the medication reaching a predetermined threshold.

17. The atomizer of claim 16, wherein the processing circuit is further configured to:
detect an unsafe level of the concentration level of the medication in the blood flow of the user; and
deactivate operation of the atomizer.

18. The atomizer of claim 16, wherein the processing circuit is further configured to:
determine vitals of the user using the plurality of spectral responses, wherein the vitals include a respiratory rate, a heart rate and a blood oxygen level.

19. The atomizer of claim 16, wherein the processing circuit is further configured to:
determine a respiratory rate of the user using one or more of the plurality of spectral responses;
determine an inhalation period and exhalation period from the respiration rate; and
control the atomizer system to increase atomization of the vapor during the inhalation period and decrease atomization of the vapor during the exhalation period.

20. The atomizer of claim 16, wherein the PPG circuit is further configured to:
generate a first spectral response of the plurality of spectral responses around a first wavelength of light reflected from the skin tissue of the user;
generate a second spectral response of the plurality of spectral responses around a second wavelength of light reflected from the skin tissue of the user;
a processing circuit configured to:
obtain a value $L_{\lambda,1}$ using the first spectral response, wherein the value $L_{\lambda,1}$ isolates the first spectral response due to pulsating blood flow;
obtain a value $L_{\lambda,2}$ using the second spectral response, wherein the value $L_{\lambda,2}$ isolates the second spectral response due to pulsating blood flow;
obtain a value $R_{\lambda1,\lambda2}$ from a ratio of the value $L_{\lambda,1}$ and the value $L_{\lambda,2}$;
determine a concentration level of the medication in the pulsating blood flow from the value $R_{\lambda1,\lambda2}$ and a calibration.

21. The atomizer of claim 15, wherein the biosensor is integrated with the atomizer or a separate device in communication with the atomizer.

22. The biosensor of claim 15, wherein the processing circuit is further configured to:
determine a concentration level of nitric oxide (NO) in blood flow of the user from at least one of the plurality of spectral responses, wherein the at least one of the plurality of spectral responses is obtained at a wavelength with a high absorption coefficient for NO; and
generate an alert in response to the concentration level of the NO reaching a predetermined threshold.

23. The biosensor of claim 22, wherein the processing circuit is further configured to:
determine a concentration level of glucose in blood flow of the user using the at least one of the plurality of spectral responses obtained at a wavelength with a high absorption coefficient for NO; and
generate an alert in response to the concentration level of the glucose reaching a predetermined threshold.

24. The biosensor of claim 23, wherein the processing circuit is further configured to:
monitor an insulin response using the at least one of the plurality of spectral responses obtained at a wavelength with a high absorption coefficient for NO.

25. The biosensor of claim 22, wherein the wavelength with the high absorption coefficient for NO includes a wavelength of approximately 390 nm.

26. The biosensor of claim 16, wherein the atomizer further includes a mask to deliver the vaper through the nose and mouth.

27. An atomizer, comprising:
a cartridge configured to hold a fluid;
an atomizer system configured to atomize the fluid in the cartridge into a vapor for inhalation;
a biosensor including:
a PPG circuit that emits light at a plurality of wavelengths directed to skin tissue of a user and generates a plurality of spectral responses around the plurality of wavelengths from light reflected from the skin tissue of the user;
a processing circuit configured to:
obtain a concentration level of a substance in blood flow of the user using the plurality of spectral responses; and control the atomizer system to increase or decrease the atomization of the fluid in response to the concentration level of the substance in the blood flow of the user.

28. The atomizer of claim 27, wherein the processing circuit is further configured to determine vitals of the user using the plurality of spectral responses, wherein the vitals include a respiratory rate, a heart rate and a blood oxygen level.

29. The atomizer of claim 27, wherein the PPG circuit is further configured to:
generate a first spectral response of the plurality of spectral responses around a first wavelength of light reflected from the skin tissue of the user;
generate a second spectral response of the plurality of spectral responses around a second wavelength of light reflected from the skin tissue of the user;
a processing circuit configured to:
obtain a value $L_{\lambda 1}$ using the first spectral response, wherein the value $L_{\lambda 1}$ isolates the first spectral response due to pulsating blood flow;
obtain a value $L_{\lambda 2}$ using the second spectral response, wherein the value $L_{\lambda 2}$ isolates the second spectral response due to pulsating blood flow;
obtain a value $R_{\lambda 1, \lambda 2}$ from a ratio of the value $L_{\lambda 1}$ and the value $L_{\lambda 2}$;
determine the concentration level of the substance in the blood flow from the value $R_{\lambda 1, \lambda 2}$ and a calibration.

30. The atomizer of claim 29, wherein the concentration level of a substance includes a blood nicotine level and wherein the first wavelength of light reflected from the skin tissue of the user includes a wavelength with a high absorption coefficient of blood nicotine at approximately 260 nm.

* * * * *